United States Patent
Yacoub

(10) Patent No.: US 11,931,081 B2
(45) Date of Patent: Mar. 19, 2024

(54) MONOAXIAL-UNIPLANAR HYBRID SCREW

(71) Applicant: GLOBUS MEDICAL, INC., Audubon, PA (US)

(72) Inventor: George Yacoub, Conshohocken, PA (US)

(73) Assignee: Globus Medical Inc., Exton, PA (US)

( * ) Notice: Subject to any disclaimer, the term of this patent is extended or adjusted under 35 U.S.C. 154(b) by 123 days.

(21) Appl. No.: 17/026,540

(22) Filed: Sep. 21, 2020

(65) Prior Publication Data
US 2022/0087721 A1 Mar. 24, 2022

(51) Int. Cl.
*A61B 17/70* (2006.01)
*A61B 17/56* (2006.01)

(52) U.S. Cl.
CPC ...... *A61B 17/7038* (2013.01); *A61B 17/7032* (2013.01); *A61B 17/7037* (2013.01); *A61B 2017/564* (2013.01)

(58) Field of Classification Search
CPC ..................................... A61B 17/7032–17/704
See application file for complete search history.

(56) References Cited

U.S. PATENT DOCUMENTS

| | | | | |
|---|---|---|---|---|
| 5,536,268 A * | 7/1996 | Griss | ..................... | A61B 17/704 606/256 |
| 5,752,957 A * | 5/1998 | Ralph | ................. | A61B 17/7037 606/76 |
| 8,430,917 B2 | 4/2013 | Rezach | | |
| 8,845,700 B2 | 9/2014 | Kwak et al. | | |
| 9,277,950 B2 | 3/2016 | Buttermann | | |
| 2005/0113830 A1* | 5/2005 | Rezach | ............... | A61B 17/7037 606/60 |
| 2005/0192571 A1* | 9/2005 | Abdelgany | ........ | A61B 17/7037 606/279 |
| 2005/0192573 A1* | 9/2005 | Abdelgany | ........ | A61B 17/7037 606/279 |
| 2006/0271193 A1* | 11/2006 | Hartmann | .......... | A61B 17/7032 623/17.11 |
| 2007/0118118 A1* | 5/2007 | Kwak | ................ | A61B 17/7037 606/279 |
| 2011/0106173 A1 | 5/2011 | Lindemann et al. | | |
| 2013/0110182 A1* | 5/2013 | Harper | ............... | A61B 17/7002 606/328 |

(Continued)

FOREIGN PATENT DOCUMENTS

EP 0880344 A1 12/1998

*Primary Examiner* — Julianna N Harvey

(57) ABSTRACT

A spinal rod anchoring device is disclosed comprising a body comprising a distal end and a proximal end, wherein a threaded bone anchor is positioned toward the distal end, and a U-shaped head portion is positioned toward the proximal end. The head portion and the threaded bone anchor are fixedly attached. The spinal rod anchoring device also comprises a saddle comprising a concave interior region wherein the interior region has an open channel. The saddle is moveably seated within the base of the head portion, and a spinal connection element is disposed on the saddle. The spinal rod anchoring device further comprises a retaining pin configured to be inserted through the channel in the saddle and secured in a groove, wherein the groove is centrally positioned within the head portion, wherein the retaining pin secures the saddle to the head portion.

20 Claims, 27 Drawing Sheets

(56) References Cited

U.S. PATENT DOCUMENTS

| | | | |
|---|---|---|---|
| 2013/0184770 A1* | 7/2013 | Buttermann | A61B 17/8605 606/305 |
| 2013/0226243 A1* | 8/2013 | Kraus | A61B 17/8605 606/279 |
| 2018/0289397 A1* | 10/2018 | Buttermann | A61B 17/7038 |
| 2022/0071664 A1* | 3/2022 | Rezach | A61B 17/7032 |

* cited by examiner

MONOAXIAL-UNIPLANAR HYBRID SCREW

BACKGROUND

Spinal fixation systems may be used in surgery to align, adjust and/or fix portions of the spinal column, i.e., vertebrae, in a desired spatial relationship relative to each other. Many spinal fixation systems employ a spinal rod for supporting the spine and for properly positioning components of the spine for various treatment purposes. Vertebral anchors, comprising pins, bolts, screws, and hooks, engage the vertebrae and connect the supporting rod to different vertebrae. The size, length and shape of the rod depend on the size, number, and position of the vertebrae to be held in a desired spatial relationship relative to each other by the apparatus. Elements of spinal fixation systems can be anchored to specific portions of the vertebra. Since each vertebra varies in shape and size, a variety of anchoring devices have been developed to facilitate engagement of a particular portion of the bone. Pedicle screw assemblies, for example, have a shape and size that is configured to engage pedicle bone.

Monoaxial screws are a type of screw in which the longitudinal axis of the threaded shank is fixed relative to the head portion, or rod slot. The longitudinal axis of the threaded shank may be aligned with the longitudinal axis of the head portion, and/or the threaded shank extends at a fixed angle relative to the head. In fixed pedicle screws, which are used in the pedicle region of the vertebra, the threaded shank can be rigidly connected to or integrally formed with the head such that the orientation of the threaded shank is fixed with respect to the head. Monoaxial screws are typically smaller in profile but less forgiving to the user when assembling the construct.

Uniplanar screws have screw heads that may deviate from the screw axis, such screws being configured for movement in one plane of the rod; they typically do not adjust to medial or lateral rod positions (like polyaxial screws). This type of screw is more commonly used in scoliosis surgery where there may be a degree of cranial or caudal angulation (such as the sagittal plane of the spine), but where there is little medial lateral screw placement deviation and the surgeon additionally needs rigid control of the screw to manipulate it in the coronal and axial plane of the spine. Similar to polyaxial screws, uniplanar screws generally are large and bulky because of the configuration of their single plane swivel mechanism.

SUMMARY

According to some embodiments, a spinal rod anchoring device comprises a body, a saddle, and a retaining pin. The body may comprise a distal end and a proximal end, and a U-shaped head portion positioned toward the proximal end, wherein the head portion may be formed by a concave base with an extension on each end of the concave base, wherein the head portion and the threaded bone anchor may be fixedly attached. The saddle may comprise a concave interior region, wherein the interior region may have an open channel therewithin, wherein the saddle may be moveably seated within the base of the head portion, and wherein a spinal connection element may be disposed on the saddle. The retaining pin may be configured to be inserted through the channel in the saddle and secured in a groove, wherein the groove may be centrally positioned within the head portion, wherein the retaining pin may secure the saddle to the head portion.

According to other embodiments, a spinal rod anchoring device may comprise a body, a saddle, a retaining pin, and a closure mechanism. The body may comprise a distal end and an proximal end, wherein a threaded bone anchor may be positioned toward the distal end, and a U-shaped head portion may be positioned toward the proximal end, wherein the head portion and the threaded bone anchor may be fixedly attached. The saddle may comprise a concave interior region, wherein the interior region may have an open channel therewithin, wherein the saddle may be moveably seated within the base of the head portion, and wherein a spinal connection element may be disposed on the saddle. The retaining pin may be configured to be inserted through the channel in the saddle and secured in a groove, wherein the groove may be centrally positioned within the base of the head portion, wherein the retaining pin may secure the saddle to the head portion. The closure mechanism may be configured to be positioned within the head portion. The saddle and the head portion may comprise two matching radii, wherein the saddle may rotate about a single axis and angulate the spinal connection element about the single axis thereof, and wherein the closure mechanism may lock the spinal connection element and the saddle in an angulation relative to the body about the single axis.

According to other embodiments, a method may comprise fastening two or more spinal rod anchoring devices into two or more vertebra. Each spinal rod anchoring device may comprise a body, a saddle, a retaining pin, and a closure mechanism. The body may comprise a distal end and an proximal end, wherein a threaded bone anchor may be positioned toward the distal end, and a U-shaped head portion may be positioned toward the proximal end, wherein the head portion and the threaded bone anchor may be fixedly attached. The saddle may comprise a concave interior region, wherein the interior region may have an open channel therewithin, wherein the saddle may be moveably seated within the base of the head portion, and wherein a spinal connection element may be disposed on the saddle. The retaining pin may be configured to be inserted through the channel in the saddle and secured in a groove, wherein the groove may be centrally positioned within the base of the head portion, wherein the retaining pin may secure the saddle to the head portion. The closure mechanism may be configured to be positioned within the head portion. The method may further comprise positioning the spinal connection element about a single axis relative to the body of a first spinal rod anchoring device, wherein the positioning comprises translating angulating the saddle within the head portion. The method may further comprise positioning the spinal connection element attached to the first rod anchoring device and interconnecting at least a second rod anchoring device with the spinal connection element.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings, which are included to provide a further understanding of the disclosure and are incorporated in and constitute a part of this application, illustrate certain non-limiting embodiments of inventive concepts. In the drawings.

DETAILED DESCRIPTION

Figure 1:
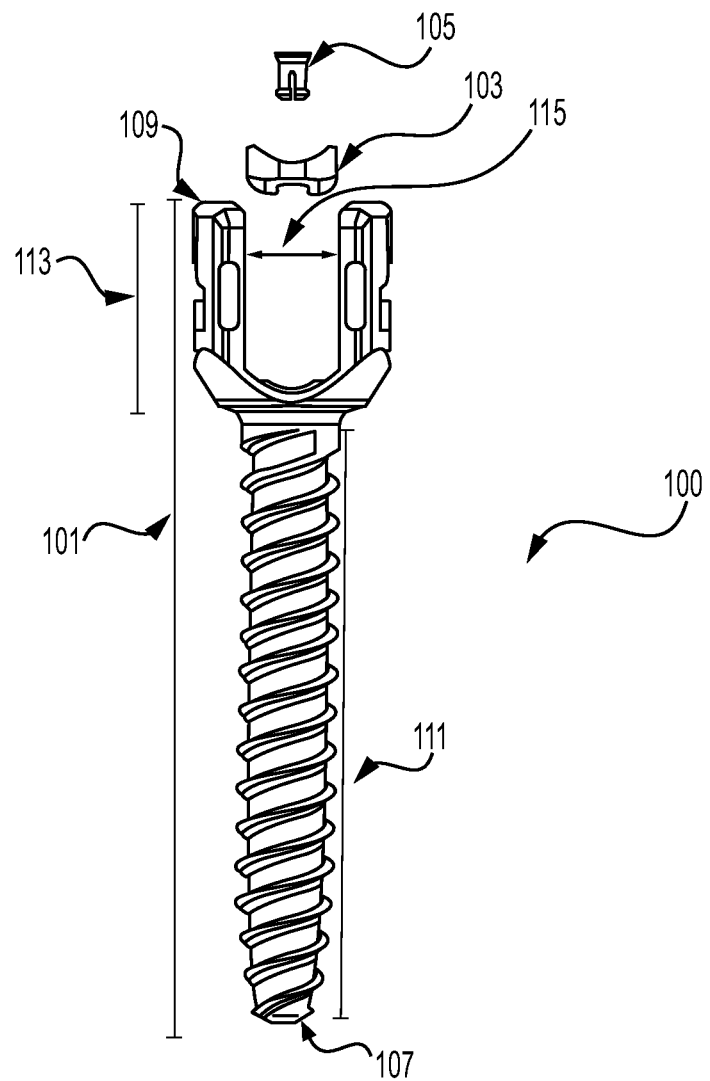
FIG. 1 illustrates portions of an exploded view of a monoaxial-uniplanar hybrid screw assembly, according to some embodiments.

It is to be understood that the present disclosure is not limited to particular devices or methods, which may, of course, vary. It is also to be understood that the terminology used herein is for the purpose of describing particular embodiments only and is not intended to be limiting. All numbers and ranges disclosed herein may vary by some amount. Whenever a numerical range with a lower limit and an upper limit is disclosed, any number and any included range falling within the range are specifically disclosed. Although individual embodiments are discussed herein, the invention covers all combinations of all those embodiments. As used herein, the singular forms "a", "an", and "the" include singular and plural referents unless the content clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to." The term "coupled" means directly or indirectly connected. If there is any conflict in the usages of a word or term in this specification and one or more patent or other documents that may be incorporated herein by reference, the definitions that are consistent with this specification should be adopted for the purposes of understanding this invention.

This disclosure relates to an apparatus for securing a spinal rod along the spine and, further, to an apparatus for locking a spinal rod in a coupling member of a spinal rod anchoring device. More particularly, the disclosed monoaxial-uniplanar hybrid screw provides a low-profile implant, rigid in three planes with "pseudo-angulation" in a single direction via saddle angulation and translation. An adjustable bone screw assembly is provided that allows for controlled adjustment of a spinal connection element, such as a spinal rod, received in a body of the bone screw assembly relative to the body of the bone screw. The adjustable bone screw assembly may allow the spinal connection element received in a receiving portion of the assembly to pivot about a single axis, while limiting movement in other directions. This disclosure relates to an apparatus having the rigidity and low profile of a monoaxial screw and the single direction angulation of a uniplanar screw, allowing the user to employ deformity techniques, such as axial derotation.

The monoaxial-uniplanar hybrid screw may allow a surgeon to rotate vertebral bodies and facilitates rod placement into the rod-receiving portion. The monoaxial-uniplanar hybrid screw may allow the surgeon to achieve an ideal orientation of the spinal rod relative to the bone screw without requiring the spinal rod to have a predetermined, fixed orientation, or necessarily be perpendicular to the longitudinal axis of the screw shank.

The exemplary monoaxial-uniplanar hybrid screw assembly of the illustrative embodiments may be employed to engage one or more spinal connection elements to bone. For example, a monoaxial-uniplanar hybrid screw may be employed to fix a spinal plate, rod, and/or cable to a vertebra of the spine. Although the disclosed exemplary monoaxial-uniplanar hybrid screw assemblies are designed primarily for use in spinal applications, and specifically the pedicle region of a vertebra, one skilled in the art will appreciate that the structure, features and principles of the exemplary monoaxial-uniplanar hybrid screw assemblies, as well as the other disclosed exemplary embodiments, may be employed to couple any type of orthopedic implant to any type of bone or tissue. The monoaxial-uniplanar hybrid screw described herein facilitates the correction of the position, for example, the angular orientation, of the vertebra in which the monoaxial-uniplanar hybrid screw assembly is implanted.

The illustrative monoaxial-uniplanar hybrid screw assembly may be used to attach a non-rigid member to bone. For example, the monoaxial-uniplanar hybrid screw may be used to attach a rod, ligament, bar, cable, or other non-rigid member extending between and connecting two bone screws, for example for connecting superior and inferior vertebra. Alternatively, the monoaxial-uniplanar hybrid screw may be used to attach a rigid member to bone. While the disclosure relates to a monoaxial-uniplanar hybrid screw that receives a spinal rod that is movable about a single axis relative to the monoaxial-uniplanar hybrid screw, the disclosure is not limited to spinal rods and may be used with any suitable spinal connection element to be coupled to bone.

The monoaxial-uniplanar hybrid screw and any of its components may be constructed of a non-organic material that is durable and that can be implanted in a human body, such as titanium, stainless steel, spring steel, aluminum, Niobium, carbon fiber, ceramics, polymers, composites or any relatively hard material (e.g. titanium-aluminum-niobium-alloy). Generally, the material selected will be biocompatible, that is, compatible with the surrounding bone and tissue.

In accordance with the present disclosure, a method of spinal fixation using the monoaxial-uniplanar hybrid screw assembly, according to some embodiments, may comprise fastening two or more monoaxial-uniplanar hybrid screw assemblies into two or more vertebra, the monoaxial-uniplanar hybrid screw assembly comprising a body, wherein the body comprises a distal end and a proximal end, wherein a threaded bone anchor portion is positioned toward the distal end, and a U-shaped head portion is positioned toward the proximal end; a saddle; a retaining pin; and a closure mechanism, such as a set screw, plug, cap, or similar type of closure mechanism. The method further comprises positioning the spinal rod about the axis relative to the body of a first monoaxial-uniplanar hybrid screw assembly, wherein the positioning of the spinal rod occurs by translating and angulating the saddle within the concave recess of the head portion; and wherein the retaining pin prevents over-translating and disassembling of the saddle within the head portion. The method further comprises correcting the position of the spine by manipulating and positioning the spinal rod attached to the first monoaxial-uniplanar hybrid screw assembly and interconnecting at least a second monoaxial-uniplanar hybrid screw assembly with the spinal rod.

Referring now to FIG. 1, which illustrates portions of an exploded view of a monoaxial-uniplanar hybrid screw assembly, according some embodiments. The portions 100 shown include a body 101, a saddle 103, and a retaining pin 105. The body 101 comprises a distal end 107 and a proximal end 109, wherein a threaded bone anchor portion 111 is positioned toward the distal end, and a U-shaped head portion 113 is positioned toward the proximal end 109. The threaded bone anchor portion 111 anchors the monoaxial-uniplanar hybrid screw assembly 100 to bone (not shown). The U-shaped head portion 113 may form a receiving portion 115, such as a rod receiving portion, for receiving a spinal rod (not shown) or other spinal connection element. As illustrated, the threaded bone anchor portion 111 extends from the U-shaped head portion 113 towards the distal end 107

Figure 2A:
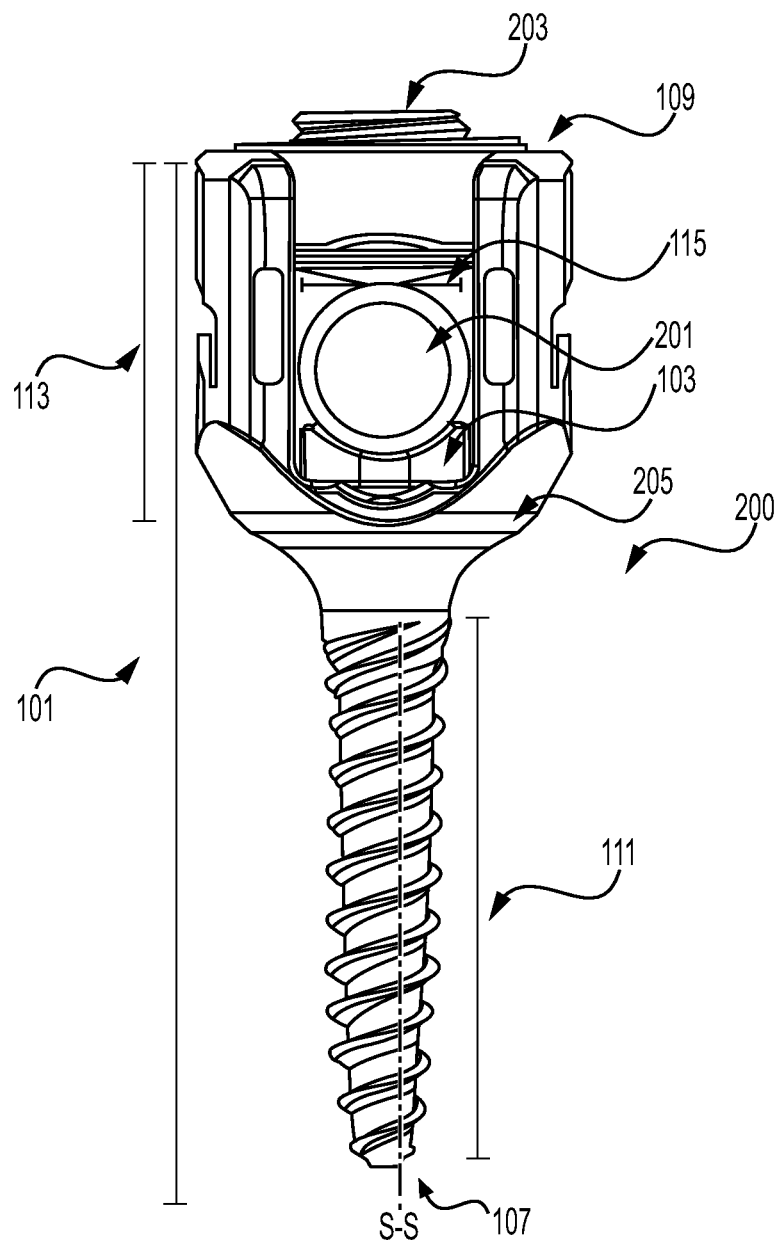
FIGS. 2A and 2B illustrate an assembled monoaxial-uniplanar hybrid screw assembly, including a spinal rod positioned therein, according to some embodiments.
Figure 2B:
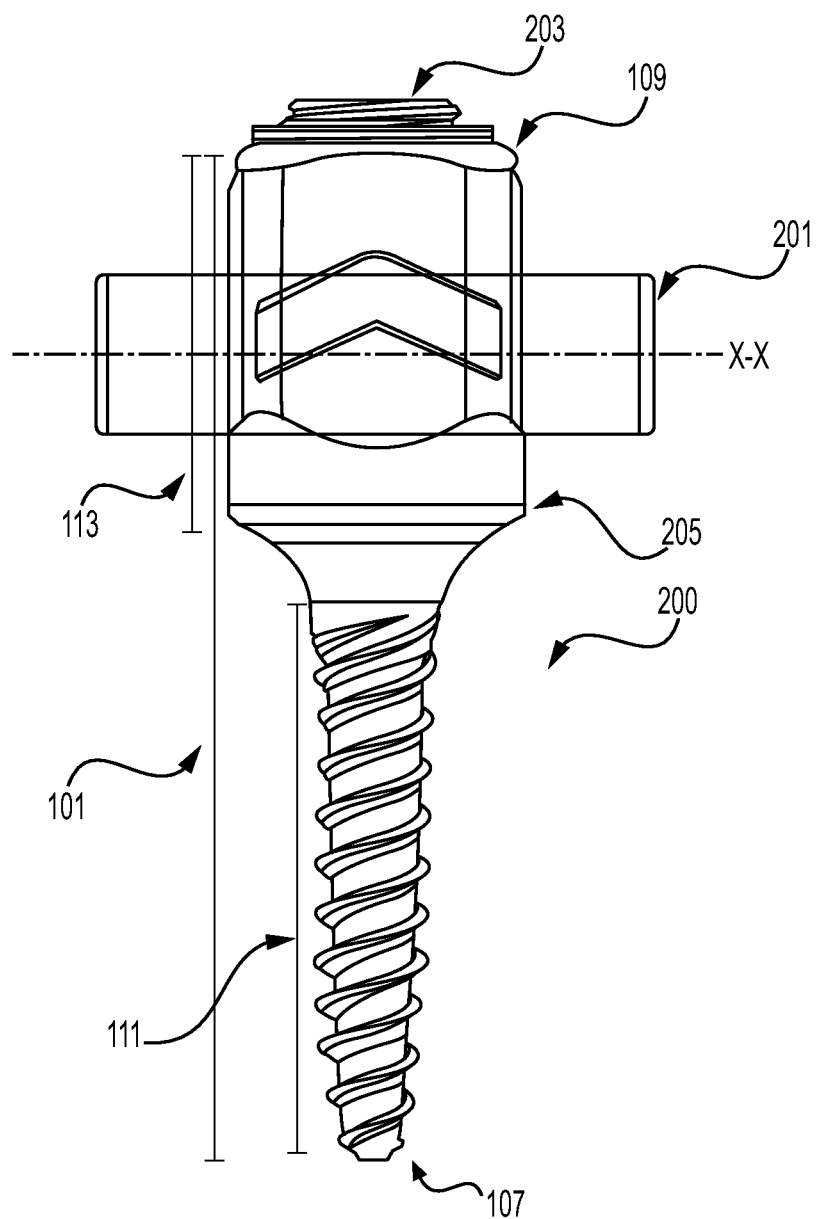

FIGS. 2A and 2B illustrate an assembled monoaxial-uniplanar hybrid screw assembly 200, including a spinal rod 201 positioned therein, according to some embodiments. The head portion 113 may form a receiving portion 115, such as a rod-receiving portion, for receiving the spinal rod 201 or other spinal connection element. A saddle 103, which may be disposed within the head portion 113 and positioned at or near the base 205 of the head portion 113, may provide seating for the spinal rod 201, thereby coupling the spinal rod 201 to a bone (not shown) anchored by the threaded bone anchor portion 111. The position of the saddle 103 may be selectively adjusted to controllably adjust the angulation of the spinal rod 201 relative to the longitudinal axis S-S of the threaded bone anchor portion 111. The saddle 103 may allow for pivoting of the spinal rod 201 about the X-X axis (e.g., shown on FIG. 2B).

The monoaxial-uniplanar hybrid screw assembly 200 further comprises a closure mechanism 203, such as a set screw, plug, cap, or similar type of closure mechanism. The closure mechanism 203 may be used to lock the spinal rod 201 or other spinal connection element into the rod-receiving portion 115 of the head 113. FIG. 2A depicts a set screw as the closure mechanism 203. The closure mechanism 203 may have any suitable size, shape, configuration and means for securing the spinal rod 201 and saddle 103 in a selected orientation relative to the body 113 of the monoaxial-uniplanar hybrid screw assembly 200. The set screw 203 may be configured to be threadably positioned within the proximal end 109 of the head portion 113 to secure and lock the spinal rod 201 in a selected configuration relative to the body 101. Moreover, the set screw 203 may provide a means of coupling the spinal rod 201 and securing the desired angulation thereof. FIG. 2B is a side view of an assembled monoaxial-uniplanar hybrid screw 200, including a spinal rod 201 movably received therein and seated in a neutral position, according to some embodiments.

Figure 3A:
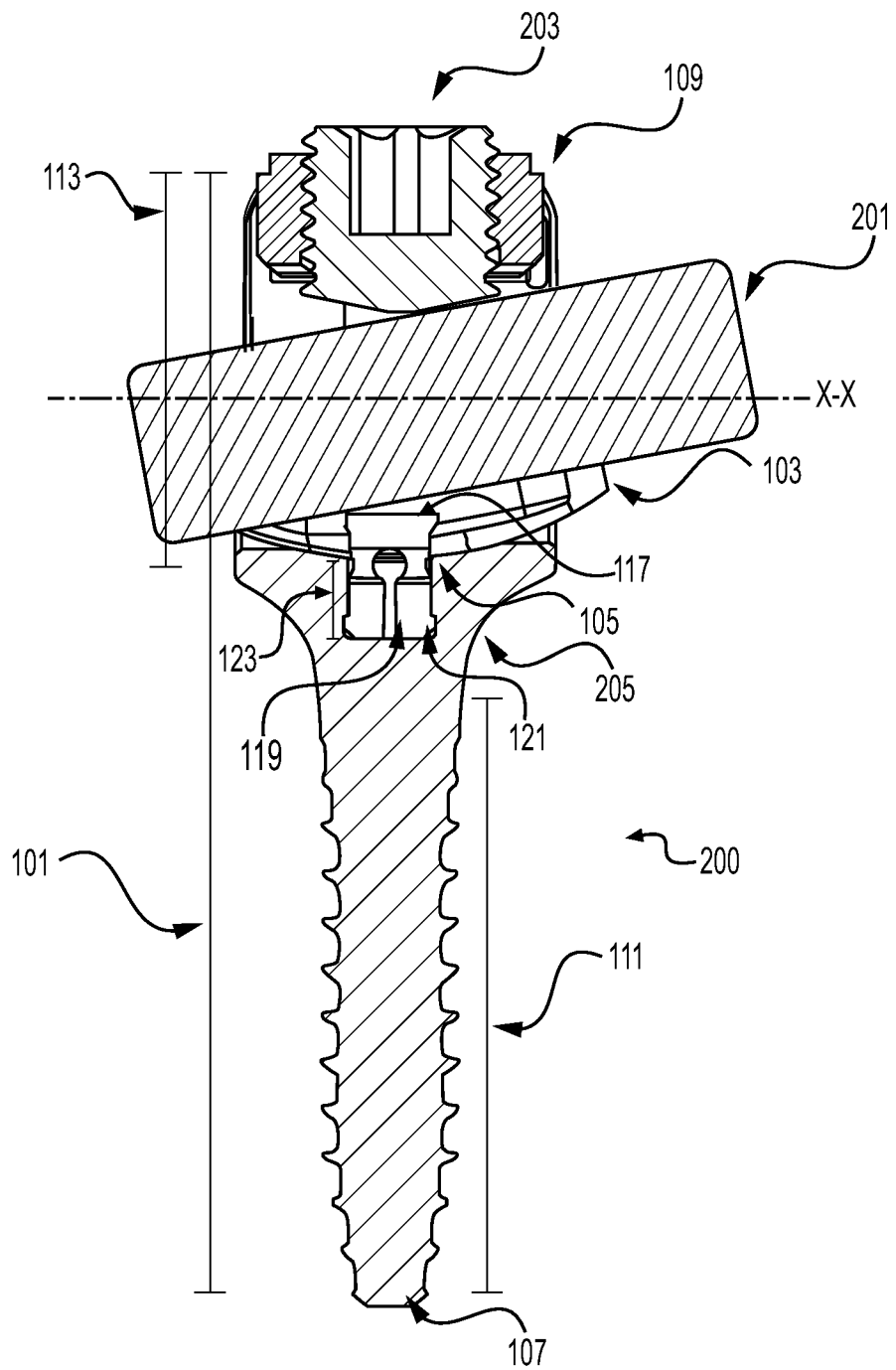
FIGS. 3A-3D illustrate cross-sectional views of assembled monoaxial-uniplanar hybrid screws, including a spinal rod positioned therein, according to some embodiments.
Figure 3B:
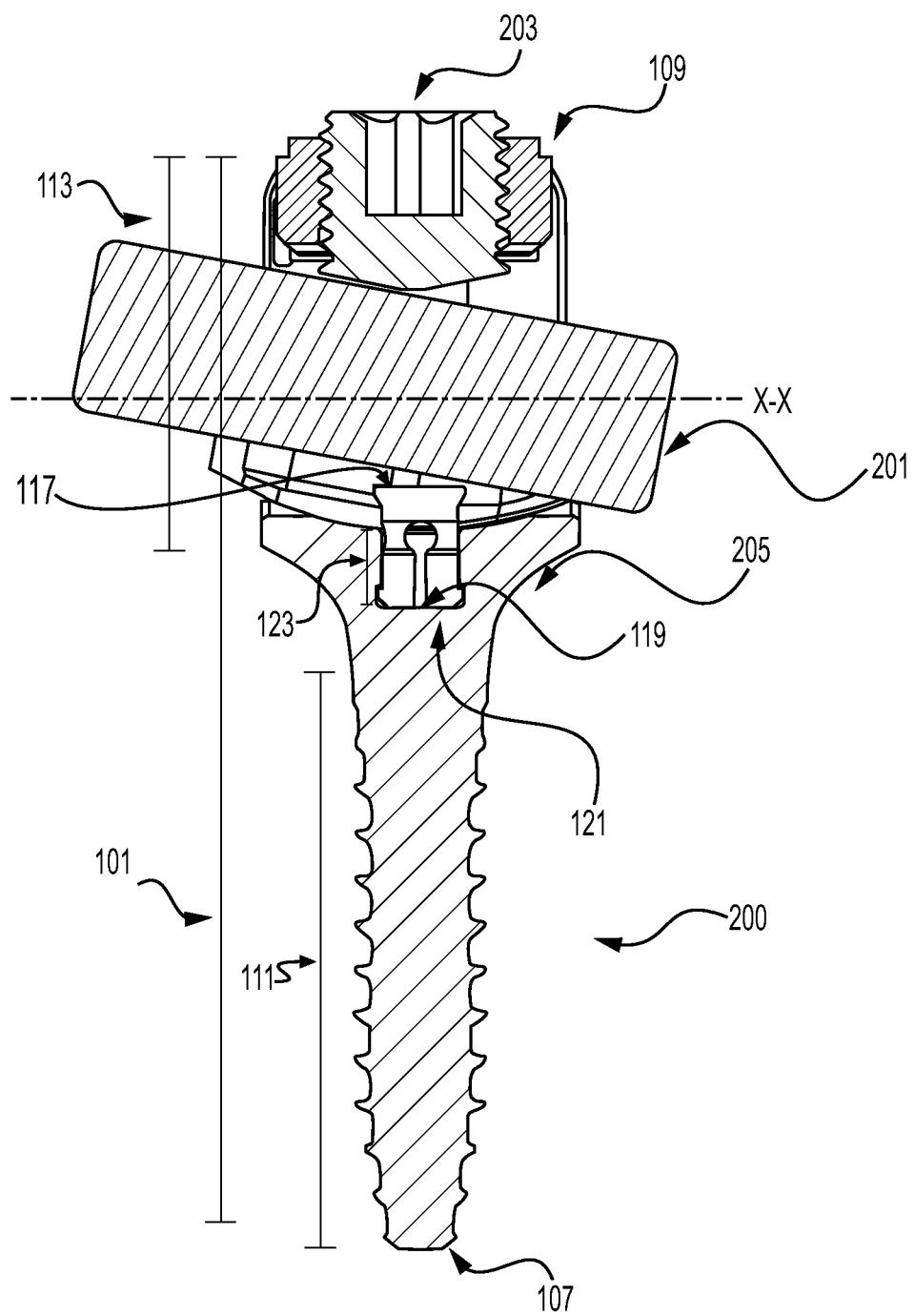
Figure 3C:
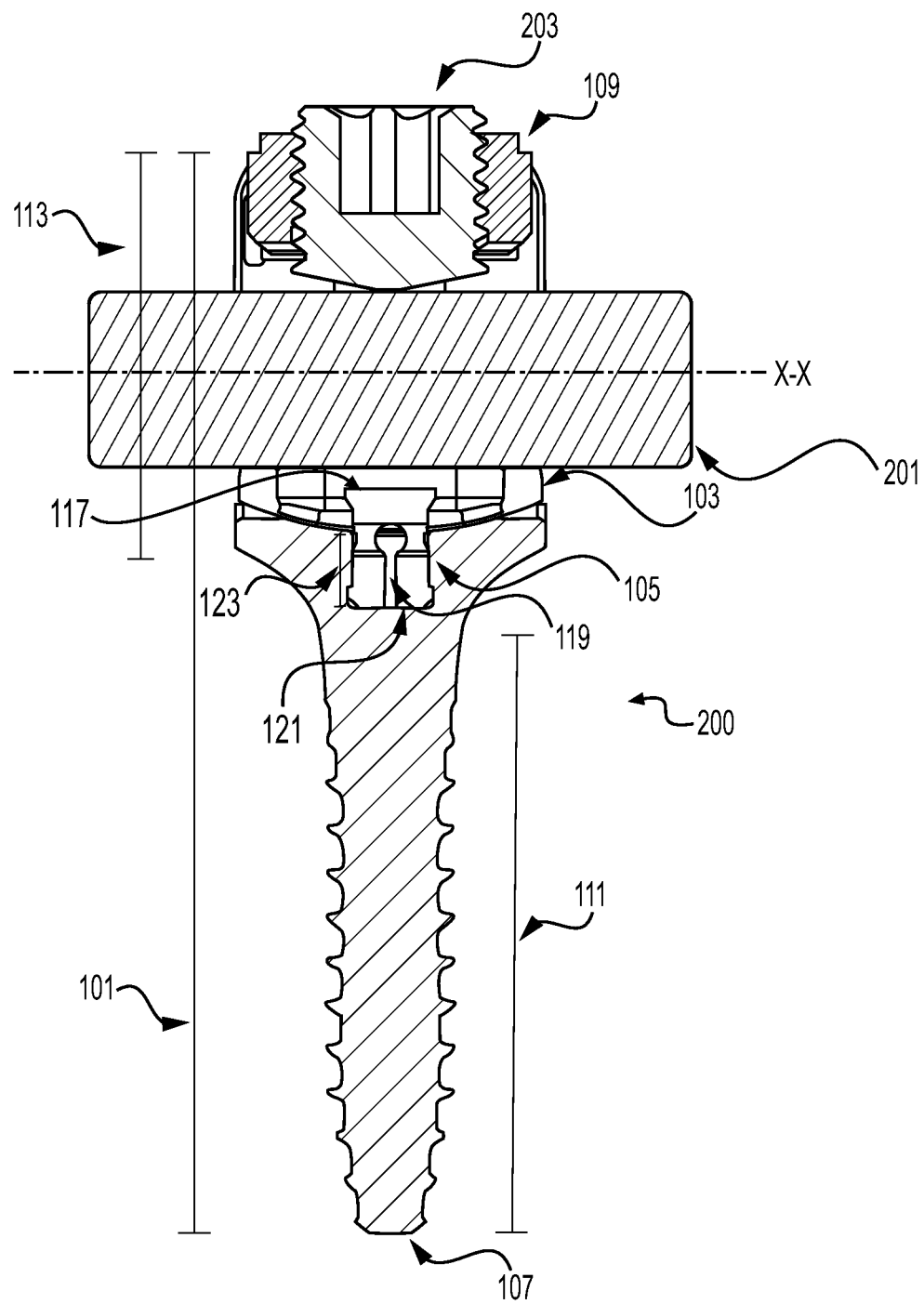
Figure 3D:
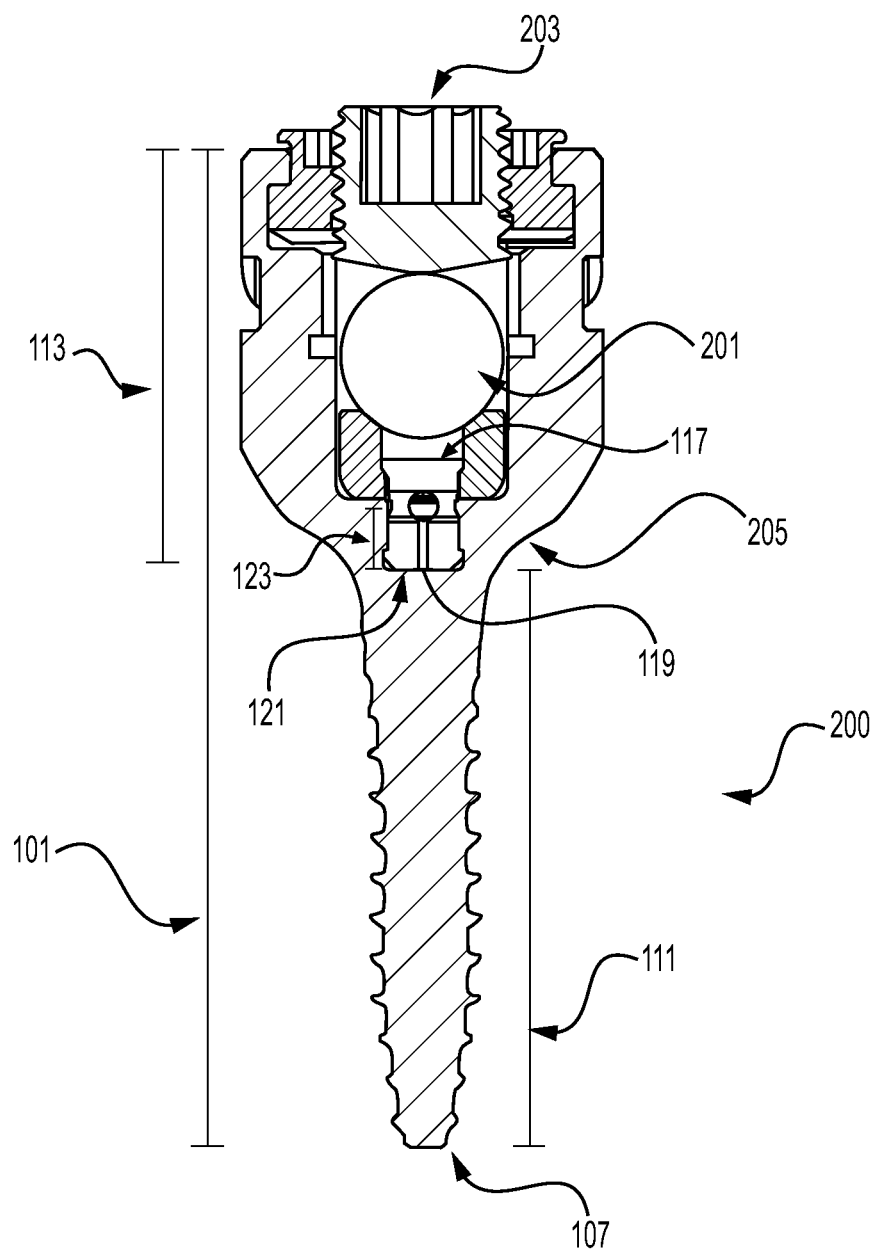

FIGS. 3A-3D illustrate cross-sectional views of assembled monoaxial-uniplanar hybrid screws, including a spinal rod 201 positioned therein, according to some embodiments. FIGS. 3A and 3B depict the monoaxial-uniplanar hybrid screw assembly 200 with the spinal rod 201 at its extreme angulation in opposing directions along the X-X axis, whereas FIG. 3C depicts a spinal rod 201 seated in the neutral position. Two matching radii on the saddle and head portion allow the saddle 103 to rock, swing, or rotate along the X-X axis within the confinements of the head portion 113. The retaining pin 105 or clip secures the saddle 103 to the head portion 113 via a conical taper at the proximal end 117 of the retaining pin 105 and one or more wire cuts 119 at the distal end 121 of the retaining pin 105; thereby allowing the retaining pin 105 to flex into a recessed area or groove 123 centrally positioned at the base 205 of the head portion 113 and extending toward the distal end 107 of the body 101 of the monoaxial-uniplanar hybrid screw assembly 200. The retaining pin 105 may prevent the saddle 103 from over translating within the head portion 113. FIG. 3D illustrates a cross-sectional view of a monoaxial-uniplanar hybrid screw assembly 200, including a spinal rod 201 movably received therein in neutral position, depicting a side view of the U-shaped head portion 113, according to some embodiments.

Figure 4A:
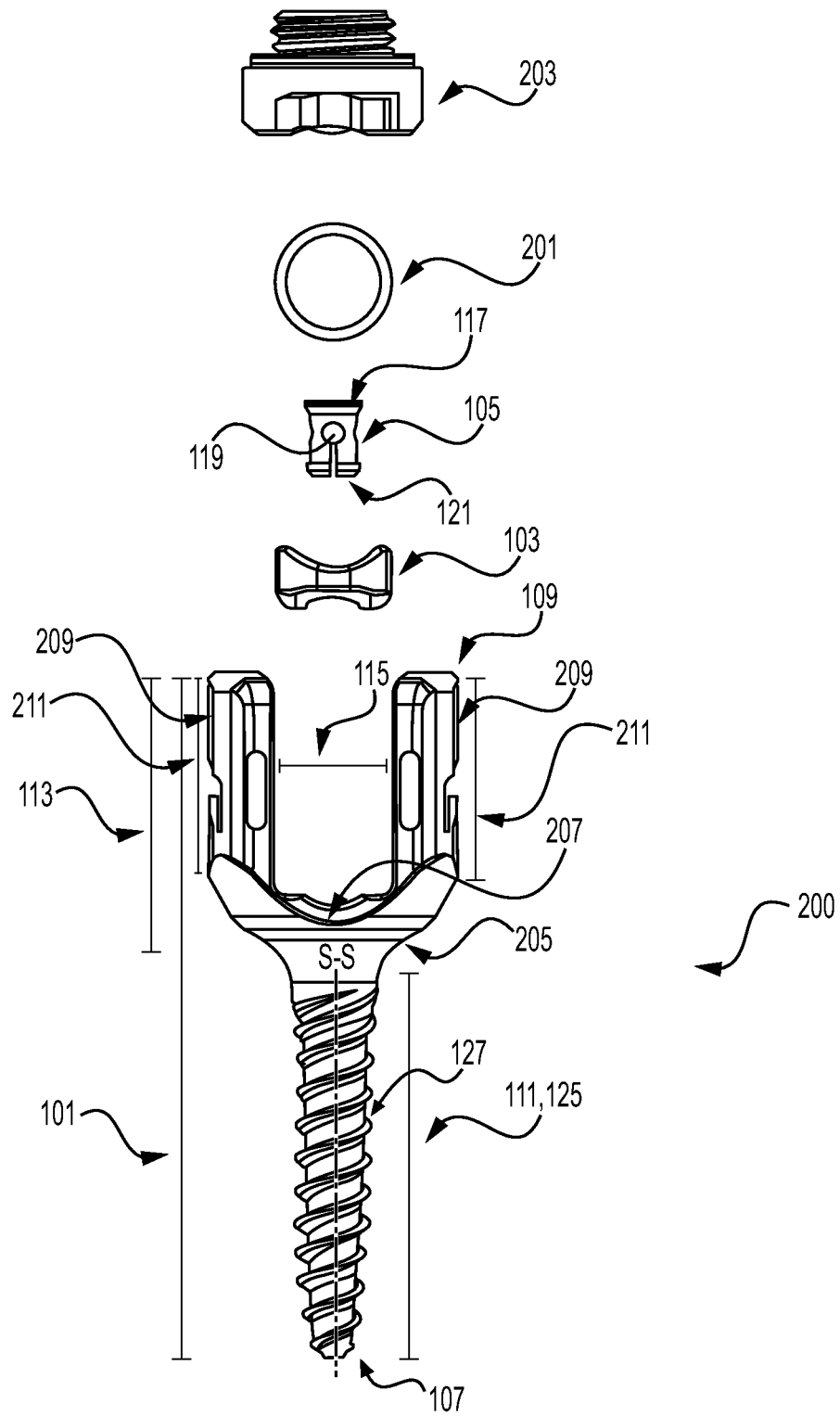
FIGS. 4A and 4B illustrate exploded views of a monoaxial-uniplanar hybrid screw assembly, including a spinal rod, according to some embodiments.
Figure 4B:
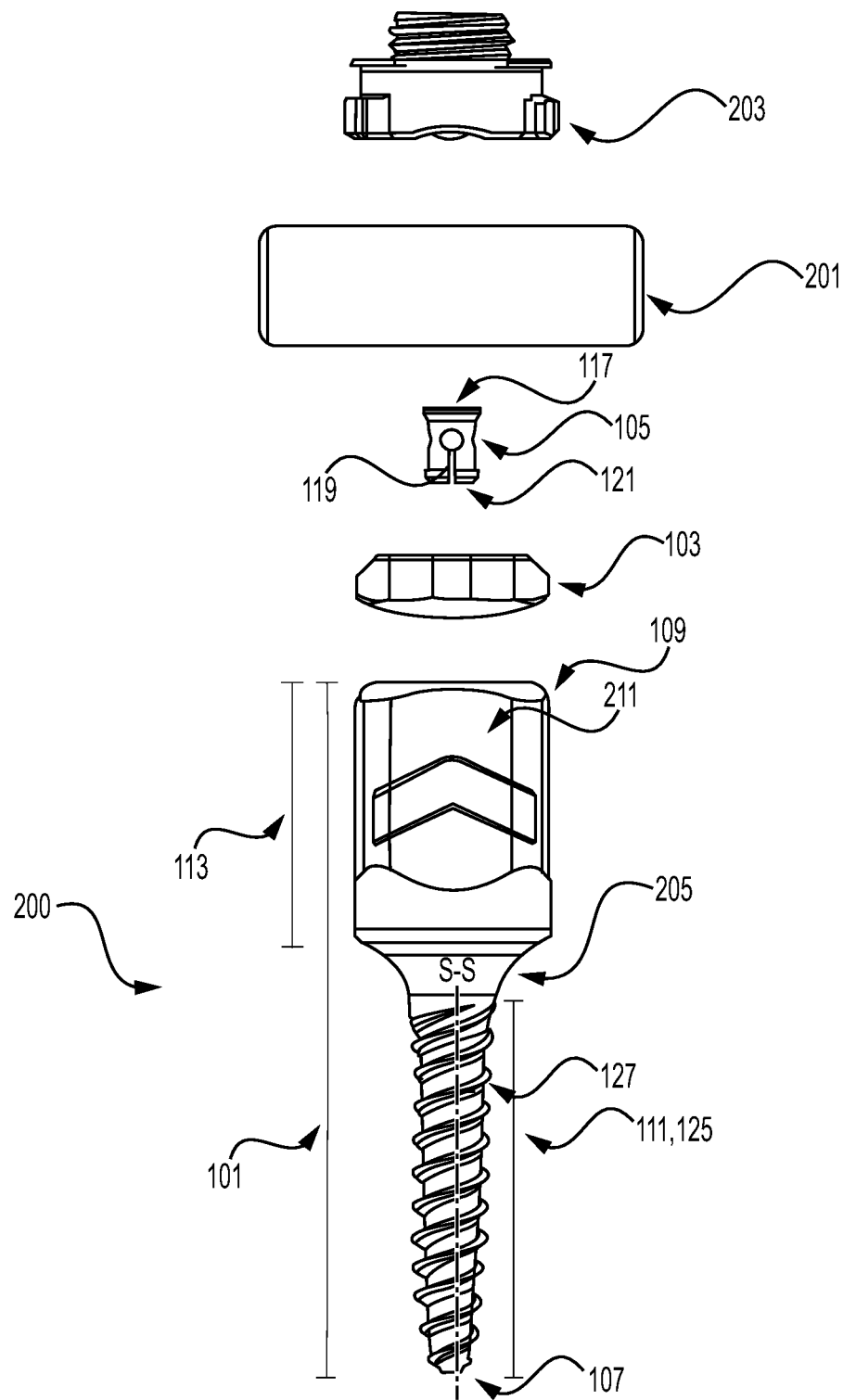

FIGS. 4A and 4B illustrate exploded views of a monoaxial-uniplanar hybrid screw assembly 200, including a spinal rod 201, according to some embodiments. FIG. 4A illustrates a side view of the monoaxial-uniplanar hybrid screw assembly 200, depicting the U-shaped head portion 113. FIG. 4B illustrates a side view of the monoaxial-uniplanar hybrid screw assembly 200, depicting closed sides 211. The threaded bone anchor comprises a shaft 125 configured to engage bone. The shaft 125 of the threaded bone anchor 111 has a shaft diameter and a longitudinal axis S-S. The shaft 125 may include one or more bone engagement mechanisms 127 to facilitate gripping engagement of the bone anchor to bone. For example, the shaft may include an external thread 127 extending along at least a portion of the shaft 125 for engaging bone. As illustrated, the external thread 127 may be a single lead thread that extends from a distal tip 127 of the shaft 125 to the head portion 113. The external thread 127 may extend along any selected portion of the shaft 125 and may have any suitable number of leads. Other suitable bone engagement mechanisms may include, but are not limited to, one or more annular ridges, multiple threads, dual lead threads, variable pitched threads, and/or any conventional bone engagement mechanism.

The head portion 113 may be configured to movably seat the saddle 103, upon which the rod 201 is disposed. The retaining pin 105 may be inserted through the saddle 103 and secured in a groove (not shown) centrally positioned at the base 205 of the head portion 113. The head portion 113 may be configured to receive a spinal rod 201 or other suitable spinal connection element. The head portion 113 may form a U-shaped opening 115, wherein the U-shaped opening 115 is formed by a concave base 207 with an extension 209 on each end of the concave base 207, whereby the extensions 209 form closed sides 211. It should be noted that some embodiments may be comprised of other suitable openings, other than U-shaped, at the proximal end 109 of the body 101 for receiving a spinal rod 201. The head portion 113 may be configured to accommodate any suitable spinal connection element 201. The head portion 113 of the monoaxial-uniplanar hybrid screw assembly 200 may be closed with a set screw 203, as illustrated, or other closure mechanism. The closure mechanism 203 secures the spinal rod 201 or other suitably configured spinal connection element within the slot 115 of the head portion 113, thereby locking the spinal rod 201 and the saddle 103 in the selected angulation within and relative to the body 101 of the monoaxial-uniplanar hybrid screw assembly 200. The head portion 113 may be fixedly or rigidly coupled to or integral with the threaded bone anchor portion 111 to form the body 101.

Figure 5A:
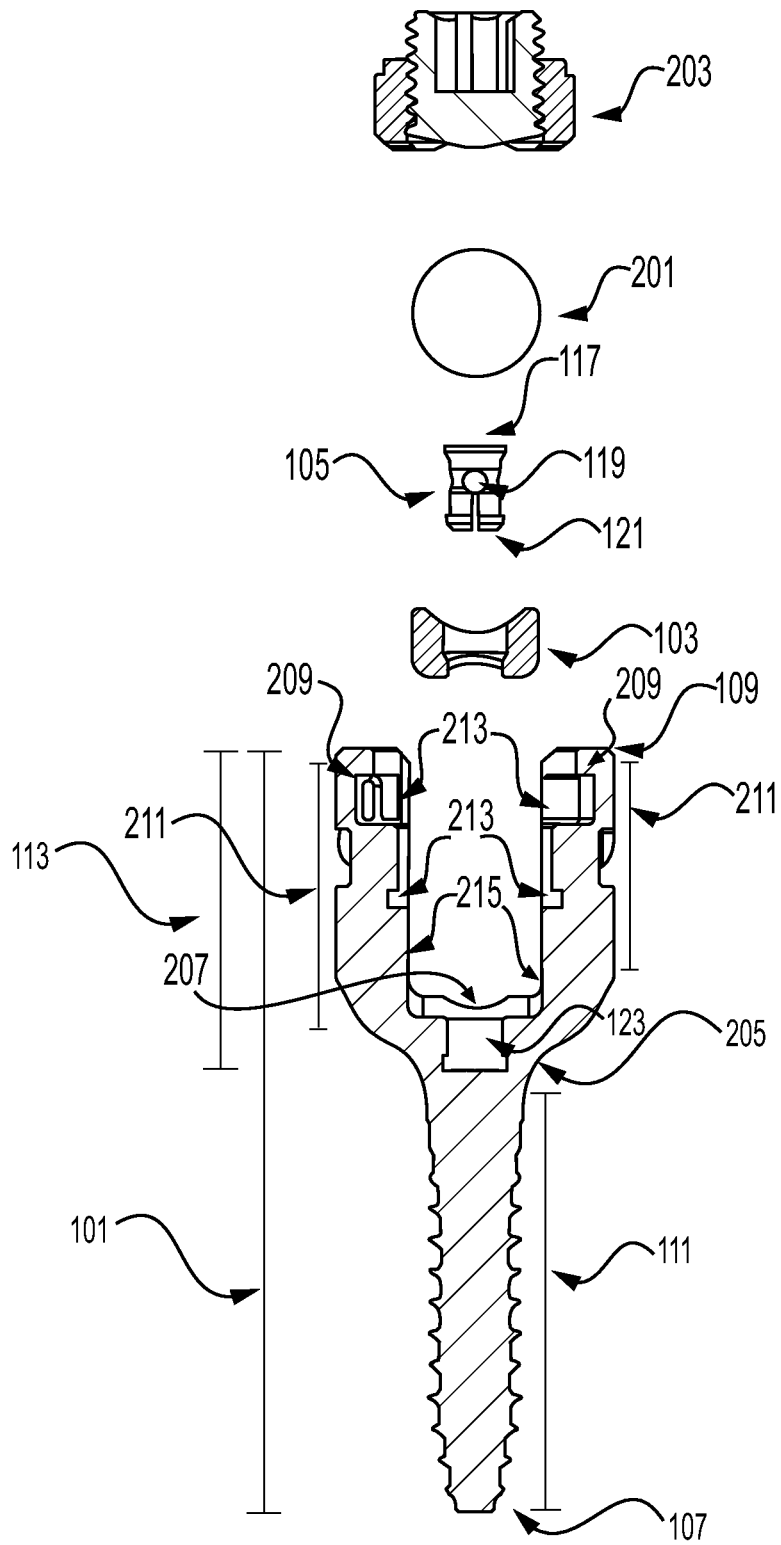
FIGS. 5A and 5B illustrate cross-sectional exploded views of a monoaxial-uniplanar hybrid screw assembly, including a spinal rod, according to one embodiment.
Figure 5B:
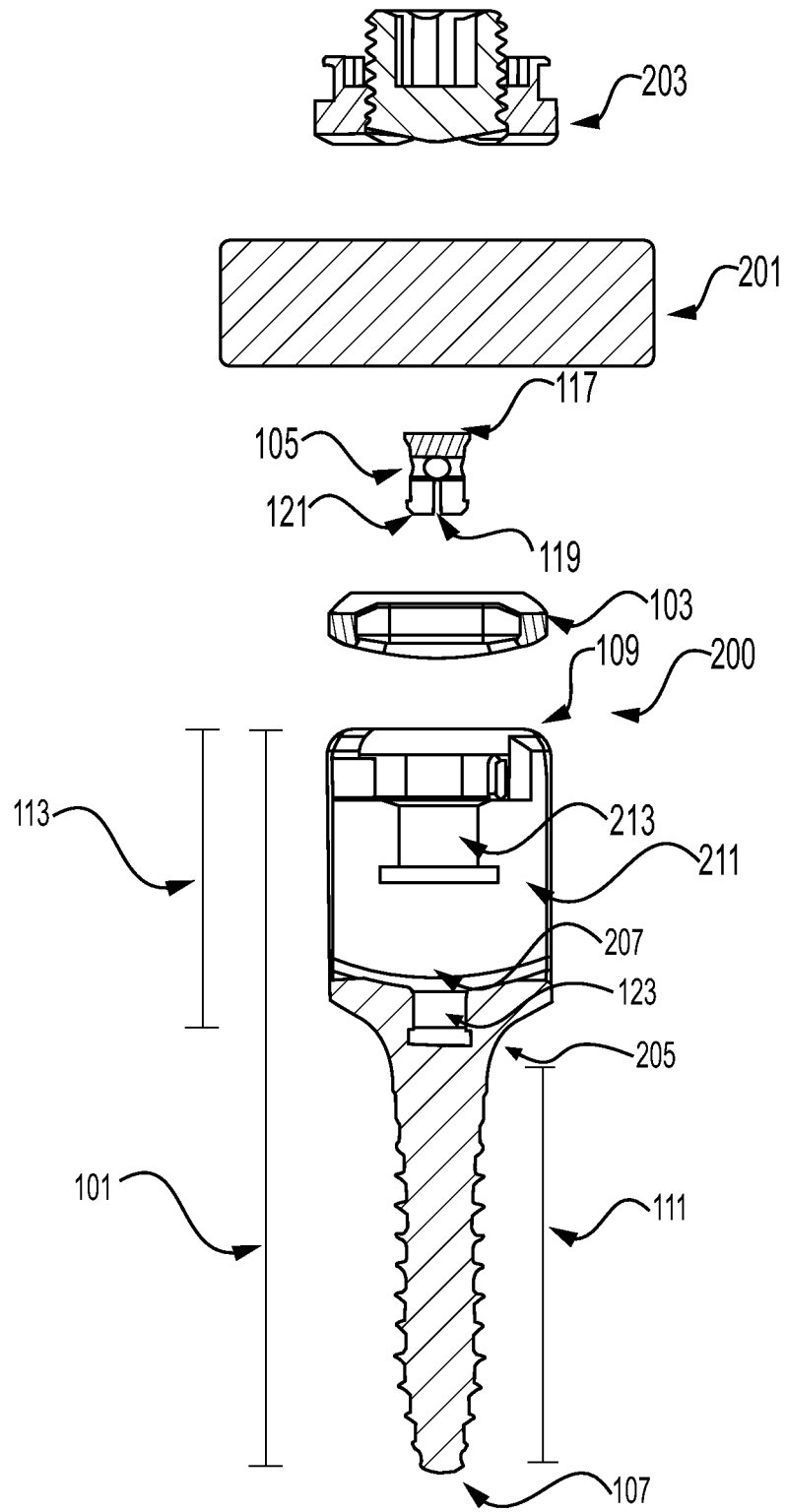

FIGS. 5A and 5B illustrate cross-sectional exploded views of a monoaxial-uniplanar hybrid screw assembly 200, including a spinal rod 201, according to one embodiment. FIG. 5A illustrates a side view of the monoaxial-uniplanar hybrid screw assembly 200, depicting the U-shaped head portion 113. The retaining pin 105 or clip secures the saddle 103 to the head portion 113 via a conical taper at the proximal end or head 117 of the retaining pin 105 and a wire cut 119 at the distal end 121 of the retaining pin 105; thereby allowing the retaining pin 105 to flex into the recessed area or groove 123 shown centrally positioned at the base 205 of the head portion 113 and extending toward the distal end 107 of the body 101 of the monoaxial-uniplanar hybrid screw assembly 200. As shown in FIG. 5A, the head portion 113 may be configured with recesses or channels 213 disposed about the internal surfaces 215 of the extensions 209. FIG. 5B illustrates a side view of the monoaxial-uniplanar hybrid screw assembly 200, depicting closed sides 211.

Figure 6A:
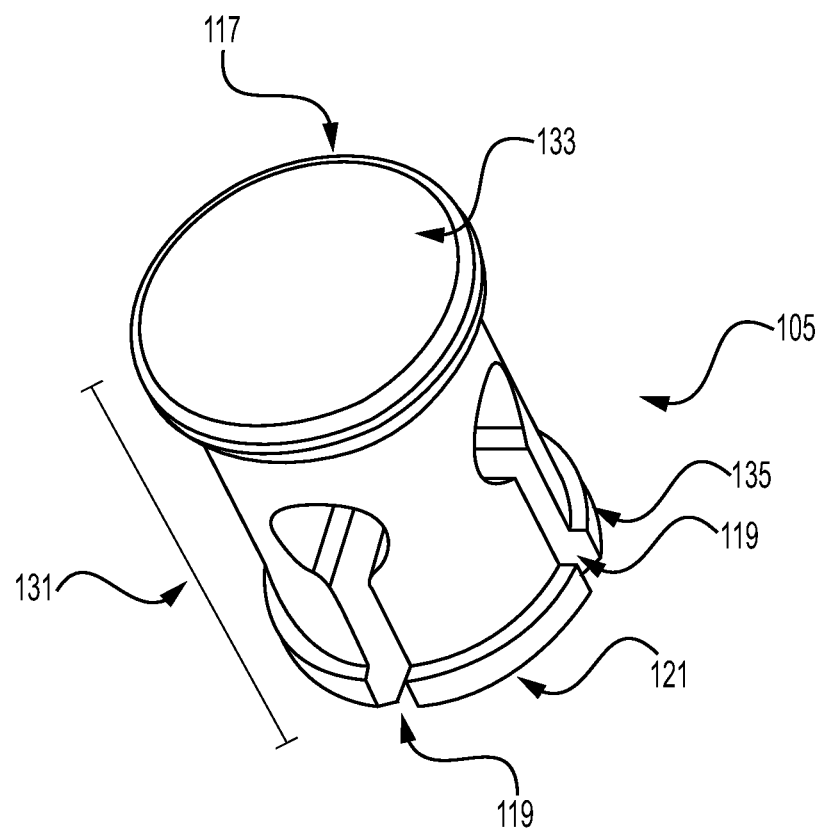
FIGS. 6A and 6B illustrate a top perspective view and a side view, respectively, of a retaining pin according to some embodiments.
Figure 6B:
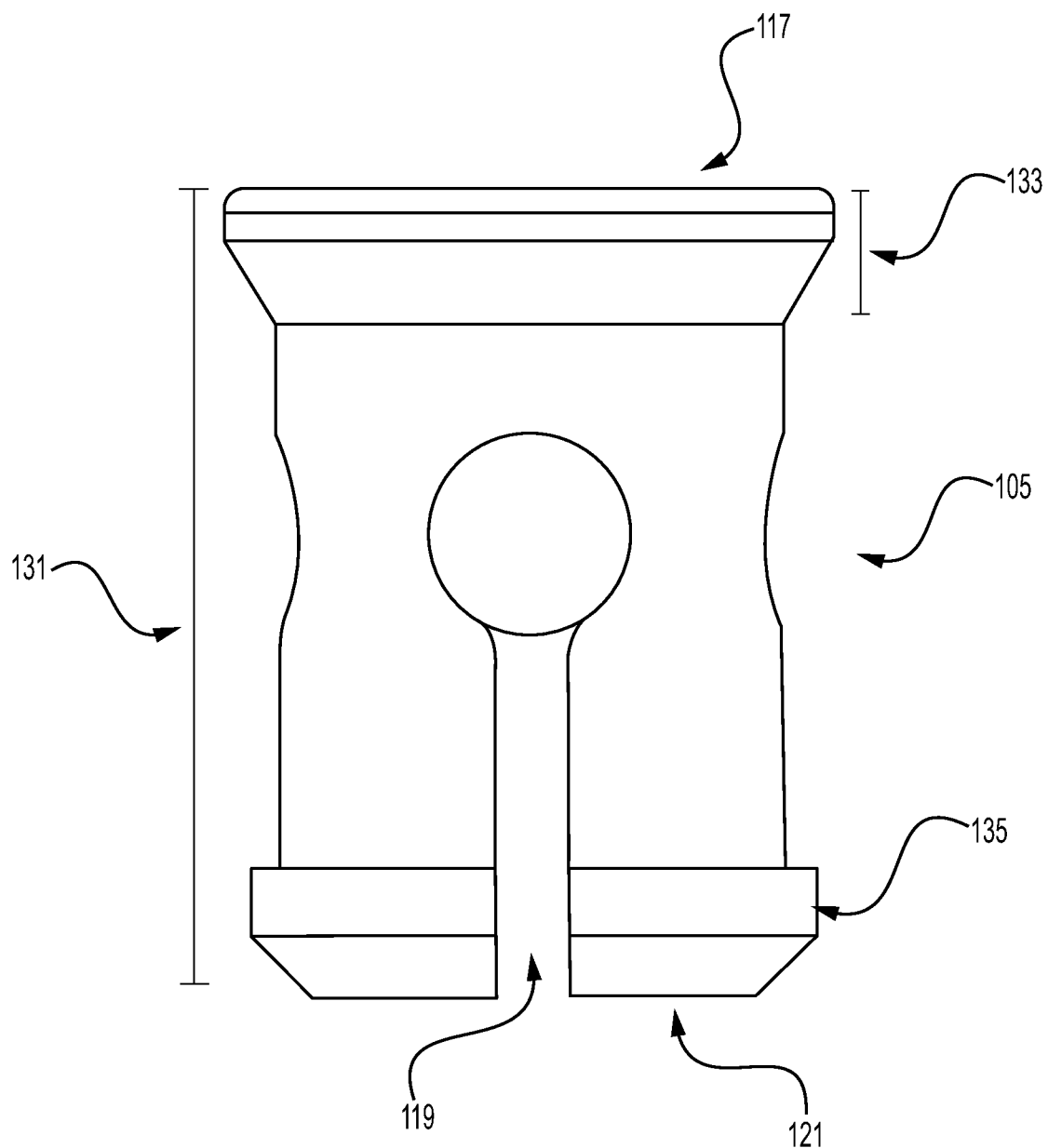

FIGS. 6A and 6B illustrate a top perspective view and a side view, respectively, of a retaining pin 105 according to some embodiments. The retaining pin 105 may comprise a body 131, wherein the body 131 may comprise a proximal end 117 and a distal end 121. The conical-shaped head 133 of the retaining pin 105 may be positioned about the proximal end 117, whereas the distal end 121 may comprise two or more wire slits 119, wherein the shape of the slits 119 may vary and may include a keyhole shape, as shown in FIGS. 6A and 6B. The distal end 121 of the retaining pin 105 may include an extension or lip 135 disposed about at least a portion of the distal end 121. The shape of the head 133 of the retaining pin 105 may be conical (as shown), circular, square, rectangular, heptagonal, octagonal, pentagonal, hexagonal, and the like. The overall shape of the body 131 of the retaining pin 105 may be cylindrical (as shown), a pentagonal prism, a hexagonal prism, and the like. The retaining pin 105 may be configured to fit within the saddle 103, thereby connecting and securing the saddle 103 to the head portion 113 of the monoaxial-uniplanar hybrid screw assembly 200. The retaining pin 105 may prevent the saddle 103 from over translating within the head portion 113. The conical taper at the head 133 of the retaining pin 105 and the wire cuts 119 about the distal end 121 of the retaining pin 105 allow the retaining pin 105 to flex into a groove or recess 123 centrally positioned about the base 205 of the head portion 113 of the monoaxial-uniplanar hybrid screw assembly 200.

Figure 7A:
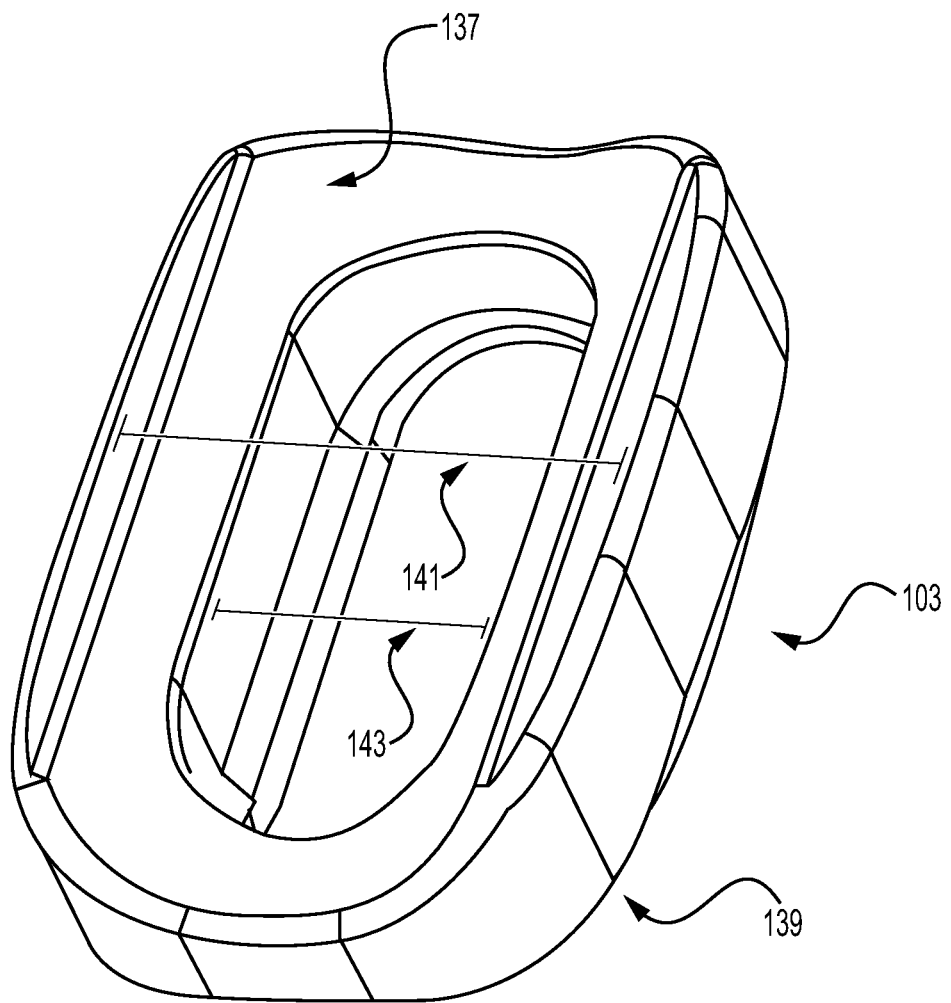
FIGS. 7A, 7B, 7C, 7D, 7E, and 7F illustrate cross-sectional isometric views of the saddle 103, according to some embodiments.
Figure 7B:
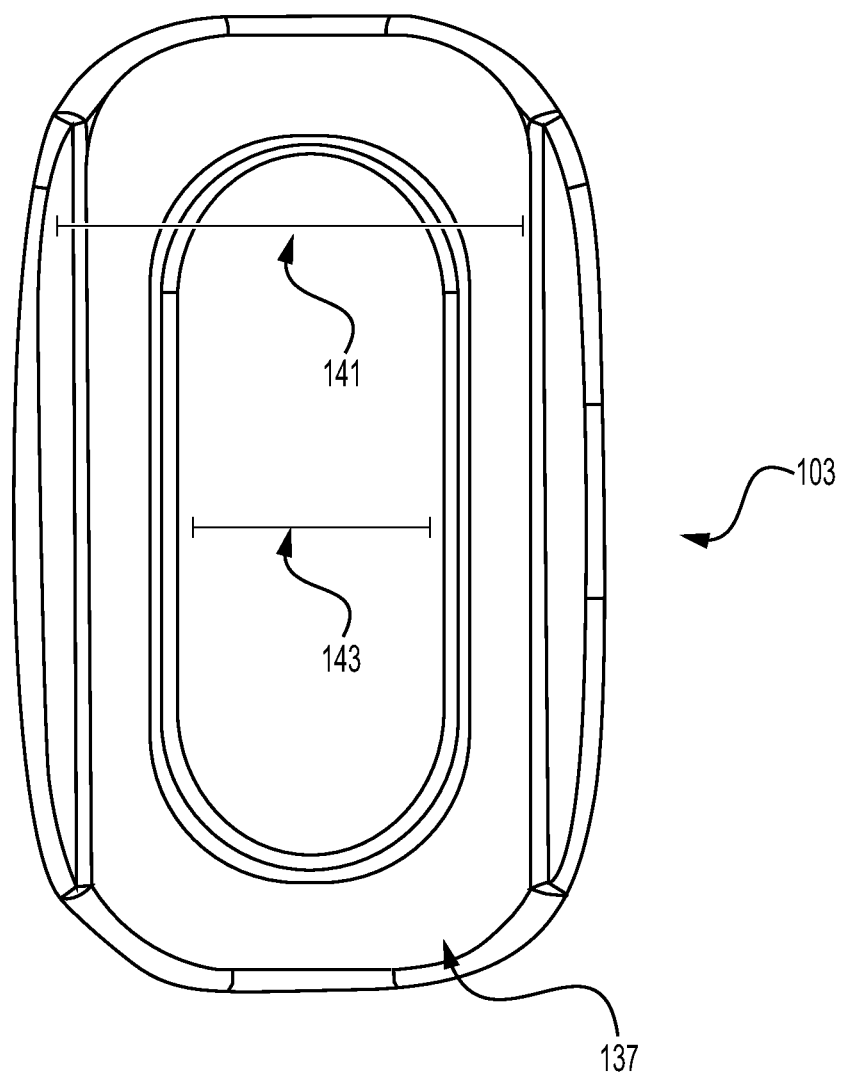

FIGS. 7A, 7B, 7C, 7D, 7E, and 7F illustrate alternative views of a saddle 103, according to some embodiments. FIG. 7A is a top isometric view of the saddle 103, according to some embodiments. FIG. 7B is a top view of the saddle 103. The saddle 103 comprises an upper surface 137 and a lower surface 139. In some embodiments, the profile of the upper surface 137 of the saddle 103 compliments or matches the profile of the spinal rod 201 to allow seating of the spinal rod 201 thereon. The shape of the saddle 103 may include, but may not be limited to, rectangular, rectangular with curved edges, stadium shaped, or oval shaped. The saddle may have a concave interior region 141, wherein the interior region 141 may have a cut-out or open channel 143 therewithin.

Figure 7C:
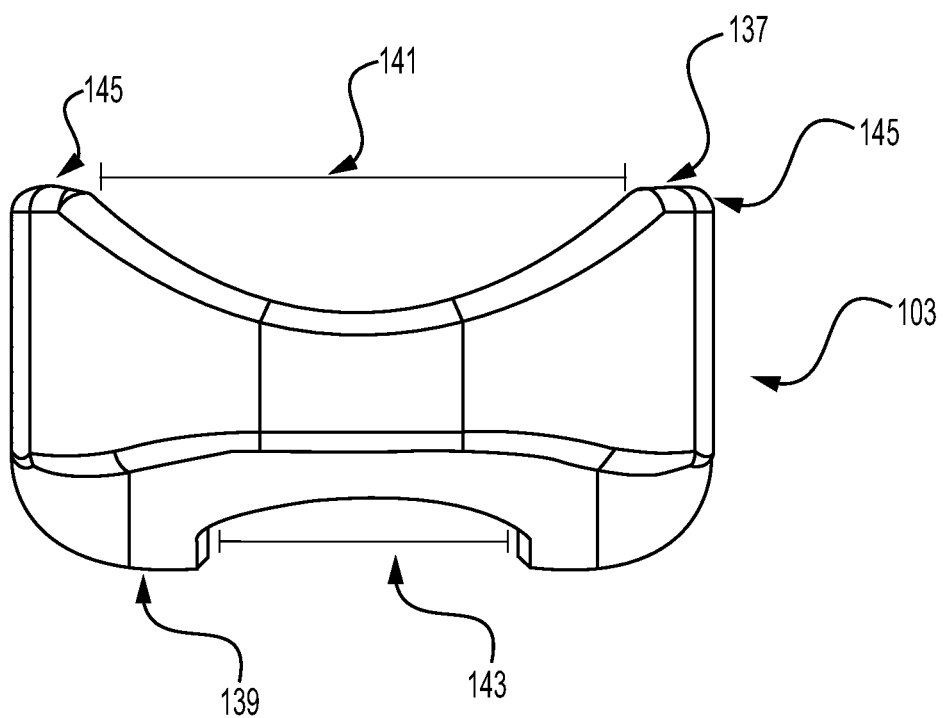
Figure 7D:
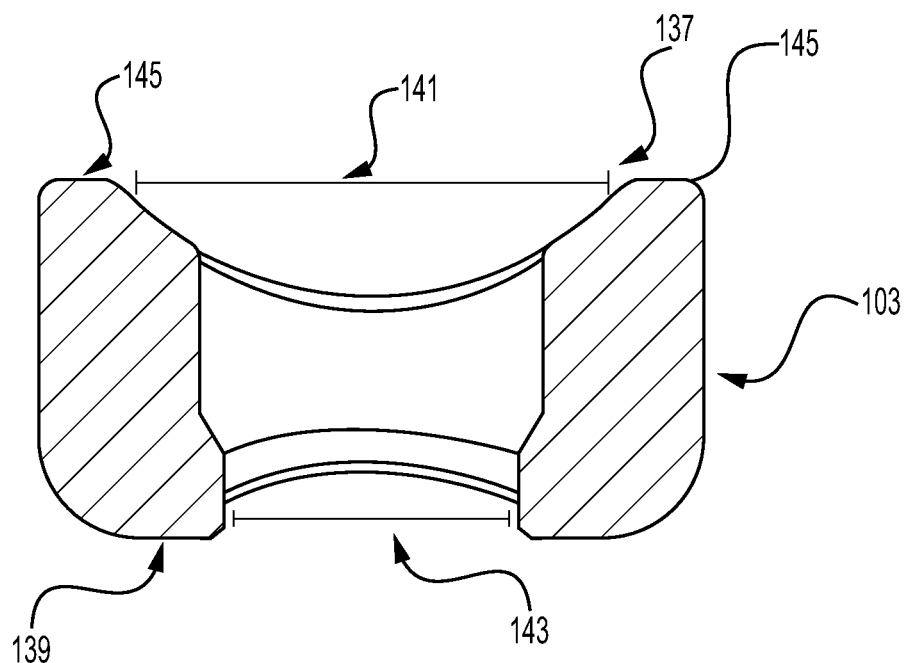
Figure 7E:
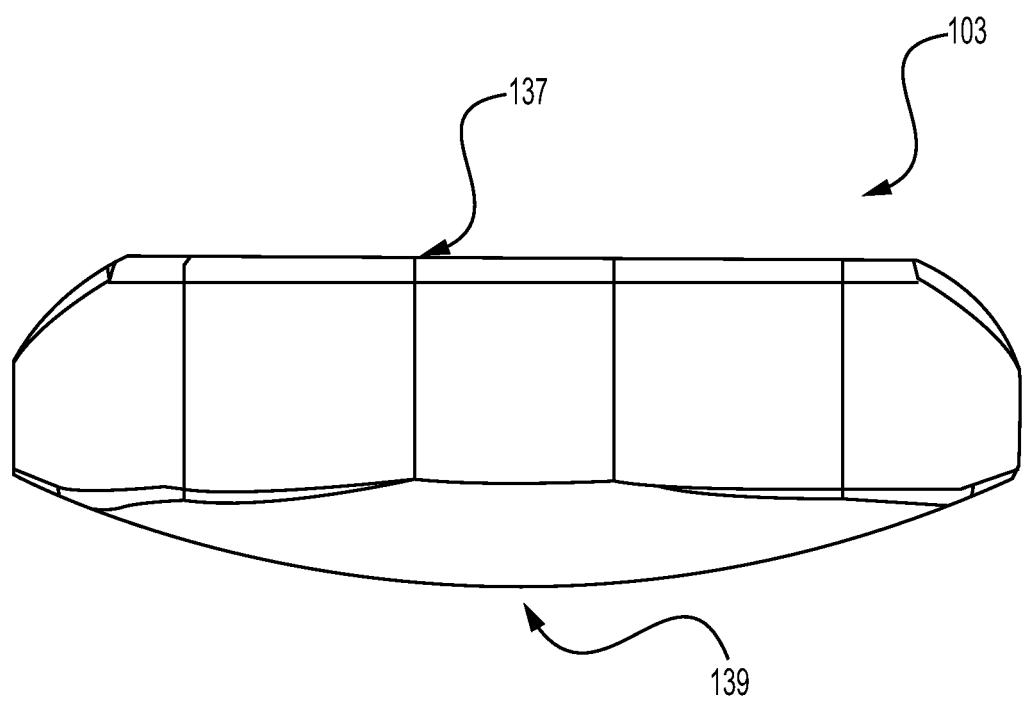
Figure 7F:
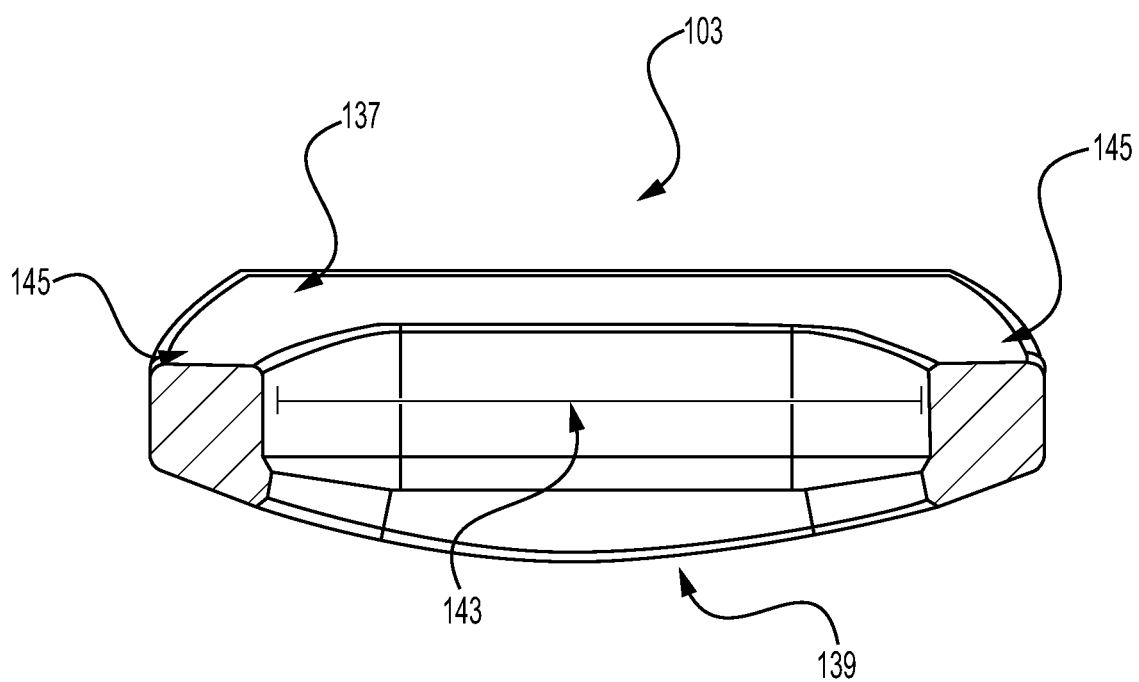

FIGS. 7C and 7D illustrate right/left side and right/left cross-sectional isometric views of the saddle 103, according to some embodiments. As shown, the lower surface 139 of the saddle 103 may have a convex, curved shape (See 7E and 7F). FIGS. 7E and 7F illustrate a front/rear perspective view and front/rear cross-sectional perspective view of the saddle 103, respectively. FIGS. 7E and 7F illustrate the convex curvature of the lower surface 139 of the saddle 103.

The spinal rod 201 may be disposed upon the upper surface 137 the saddle 103, as the saddle 103 allows for pivoting of the spinal rod 201 about the X-X axis relative to the body 101 of the monoaxial-uniplanar hybrid screw assembly 200. The concave recess 207 at the base 205 of the head portion 113 of the body 101 of the monoaxial-uniplanar hybrid screw assembly 200 is configured to receive the convex curvature of the lower surface 139 of the saddle 103. The convex curvature of the lower surface 139 of the saddle 103 allows pivoting of the saddle 103 within the recess 207 along a single axis, wherein the retaining pin 105, inserted within and through the cut-out or channel 143, secures the saddle 103 in place, thereby allowing for single axis rotation.

Figure 8A:
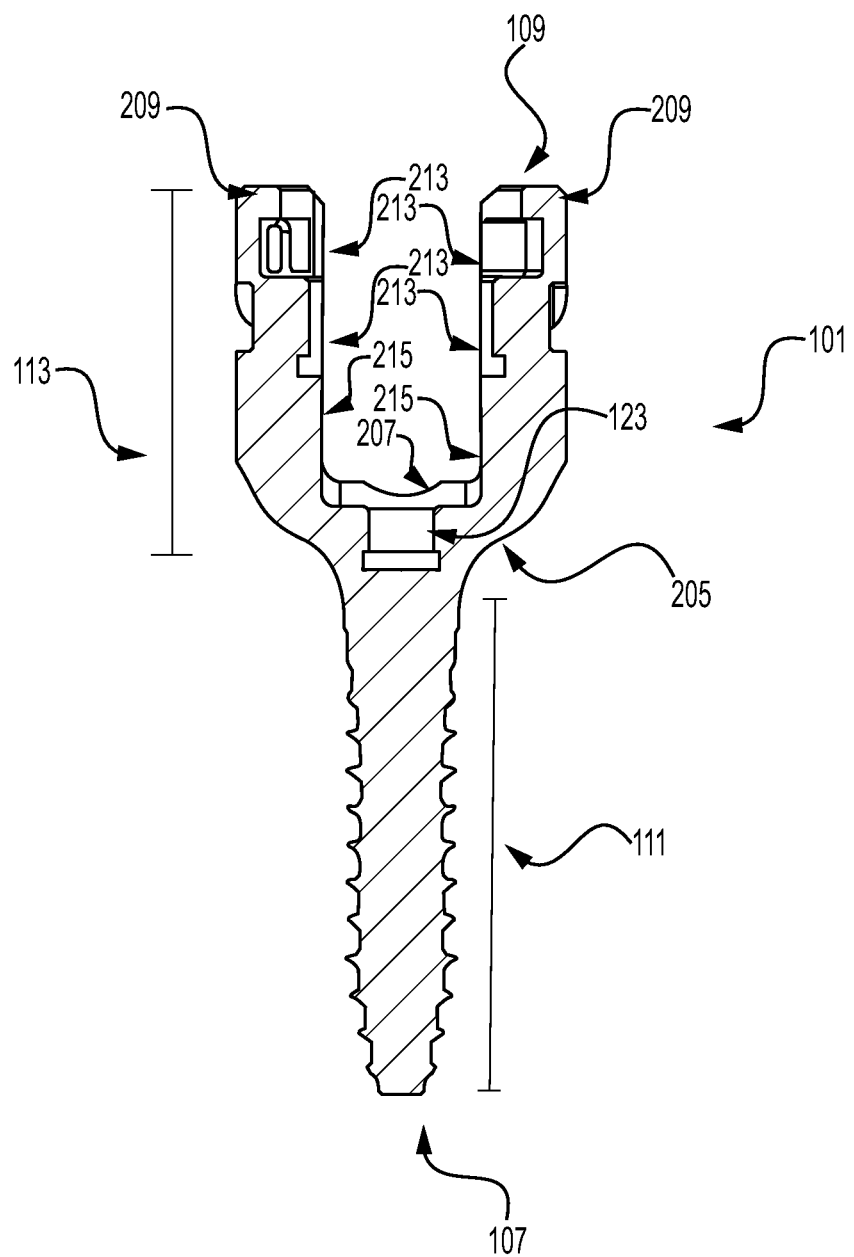
FIGS. 8A and 8B illustrate cross-sectional views of the body of a monoaxial-uniplanar hybrid screw assembly, according to some embodiments.
Figure 8B:
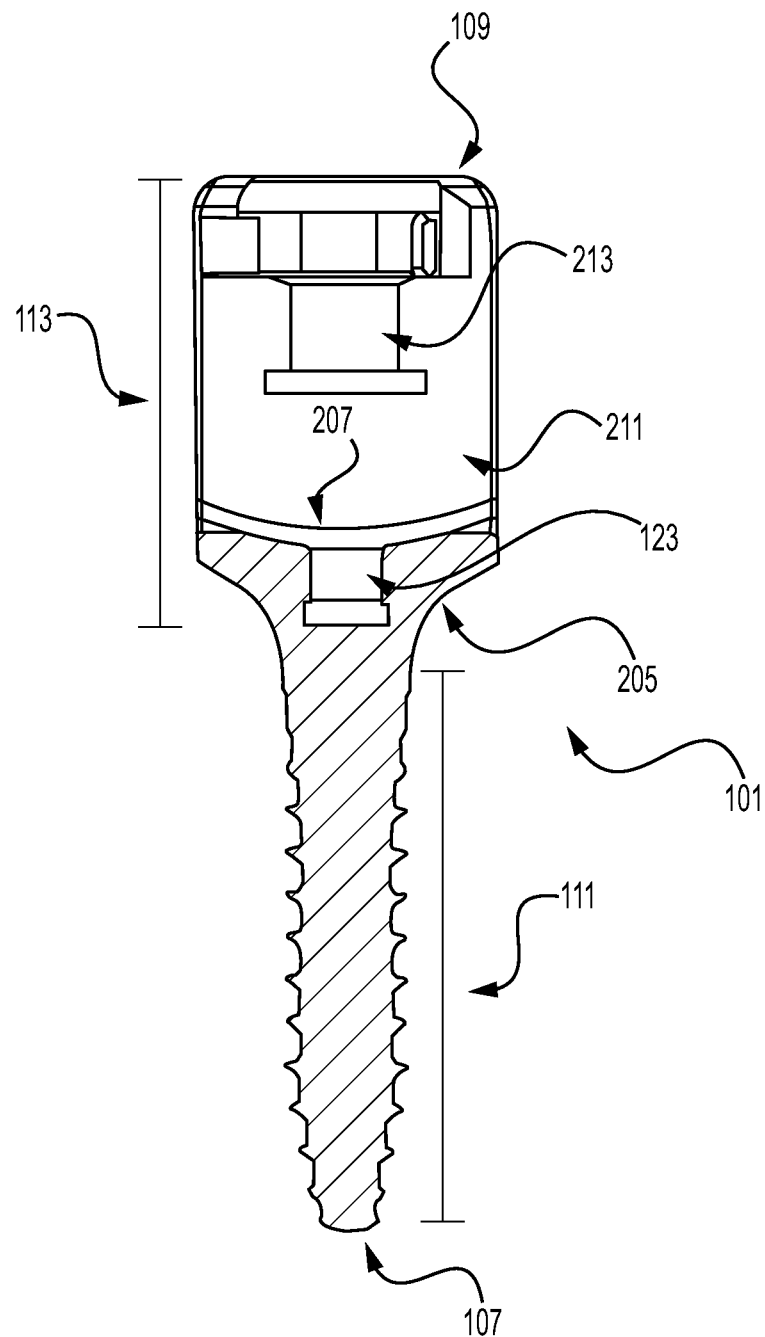

FIGS. 8A and 8B illustrate cross-sectional views of the body 101 of a monoaxial-uniplanar hybrid screw assembly, according to some embodiments. FIG. 8A illustrates a side cross-sectional view of the body 101 of the monoaxial hybrid screw assembly 200, depicting the U-shaped head portion 133. The centrally positioned recess, cavity, or groove 123 configured to receive and secure the retaining pin 105 is shown. The recesses or channels 213 disposed about the internal surfaces 215 of the extension sides 209 are also shown. The recesses or channels 213 may be configured to receive and secure a closure mechanism 203 (not shown) and/or to help guide movement of the spinal rod 201 (not shown) and the saddle 103 (not shown) upon which the spinal rod 201 (not shown) is disposed. FIG. 8B illustrates a side cross-sectional view of the body 101 of the monoaxial-uniplanar hybrid screw assembly 200, depicting closed sides 211.

Figure 9A:
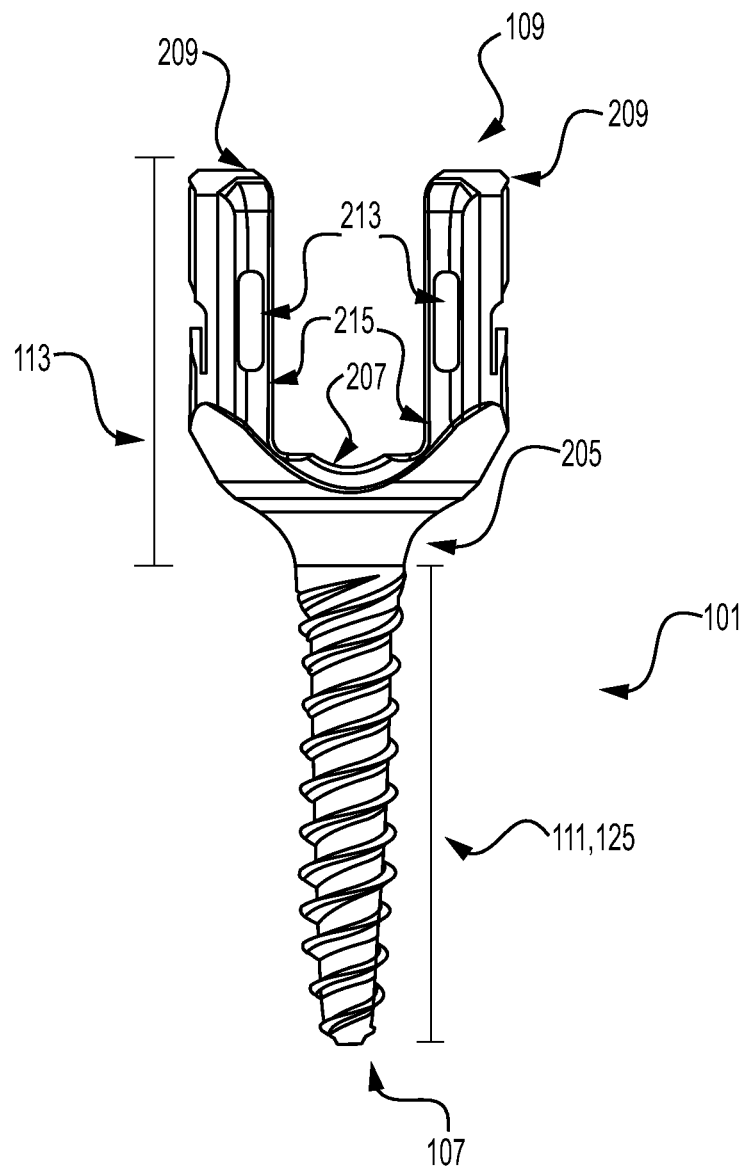
FIGS. 9A, 9B, 9C, and 9D illustrate alternative views of the body of a monoaxial-uniplanar hybrid screw, according to some embodiments.

FIGS. 9A, 9B, 9C, and 9D illustrate alternative views of the body 101 of a monoaxial-uniplanar hybrid screw, according to some embodiments. FIG. 9A is an isometric side view of the body 101 of the monoaxial-uniplanar hybrid screw assembly 200, depicting a side view of the U-shaped head portion 113.

Figure 9B:
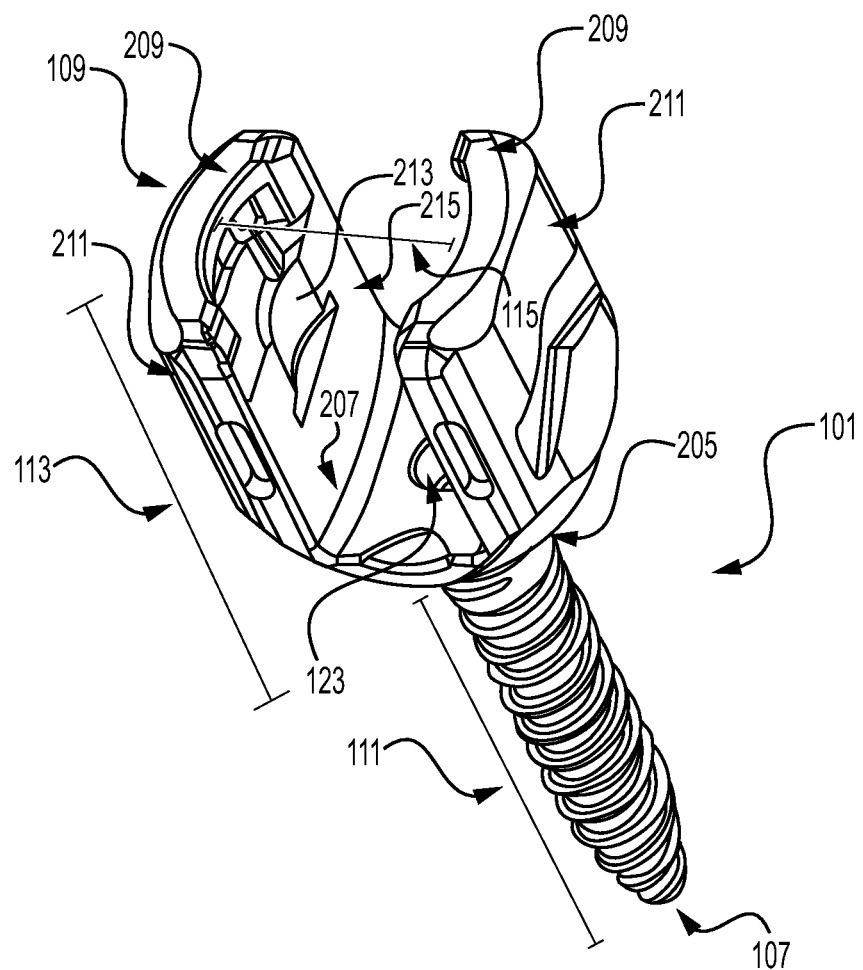

FIG. 9B is an isometric side view of a monoaxial-uniplanar hybrid screw assembly 200. The head portion 113 may form a U-shaped slot 115 or other suitable opening at the proximal end 109 of the body 101. The base 205 of the head portion 113 may be configured to seat the saddle 103 (not shown). The base 205 of the head portion 113 may also comprise a centrally positioned recess, cavity, or groove 123 configured to receive and secure the retaining pin 105. The head portion 113 may also be configured to receive a spinal rod or other suitable spinal connection element 201 and to couple the spinal rod 201 to the threaded bone anchor 111. The head portion 113 may be configured to accommodate any suitable spinal connection element 201. The opening 115 at the top of the head portion may be configured to receive a set screw 203, wherein the set screw 203 may provide a means of closing the proximal end 109 of the body 113. The set screw 203 may also provide a means of coupling and securing the spinal rod 201 and the desired angulation thereof. The head portion 113 may be fixedly or rigidly coupled to or integral with the threaded bone anchor portion 111 to form the screw body 101.

The recesses or channels 213 disposed about the internal surfaces 215 of the extension sides 209 may also help guide movement of the spinal rod 201 and the saddle 103 upon which the spinal rod 201 is disposed upon. In other embodiments, the internal surfaces 215 of the extension sides 209 may comprise threads (not shown) disposed thereupon, wherein the threads allow for threadably coupling a closure mechanism, such as a set screw (not shown).

Figure 9C:
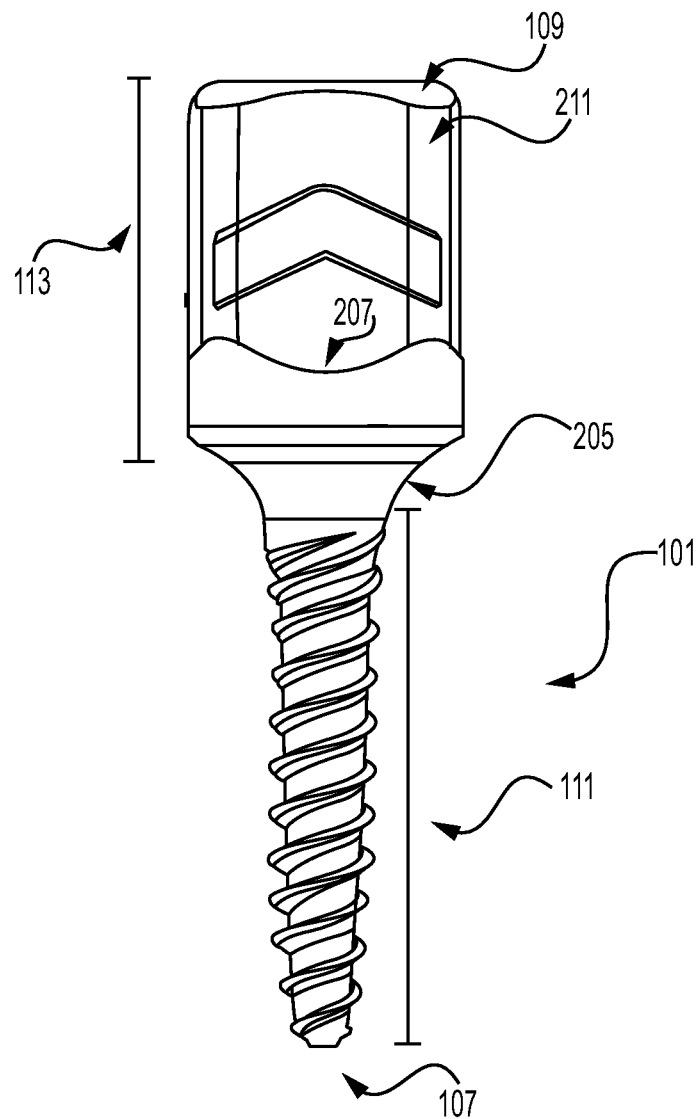
Figure 9D:
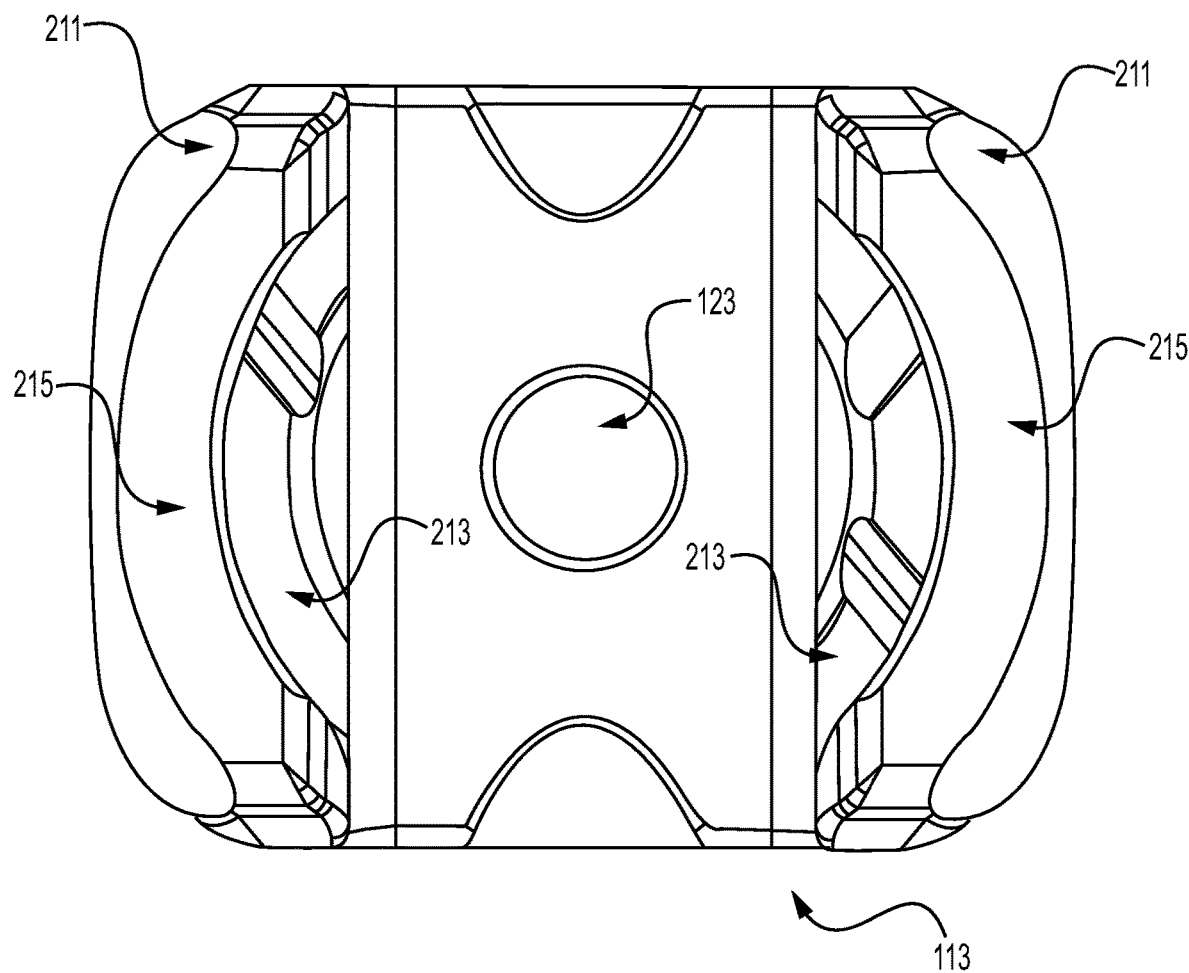

FIG. 9C is an isometric side view of the body 101 of a monoaxial-uniplanar hybrid screw assembly 200, depicting an external recess disposed on the head portion 113, according to some embodiments. FIG. 9D is an isometric top view of the head portion 113, according to some embodiments. The centrally positioned recess, cavity, or groove 123 configured to receive and secure the retaining pin 105 is shown.

Figure 10A:
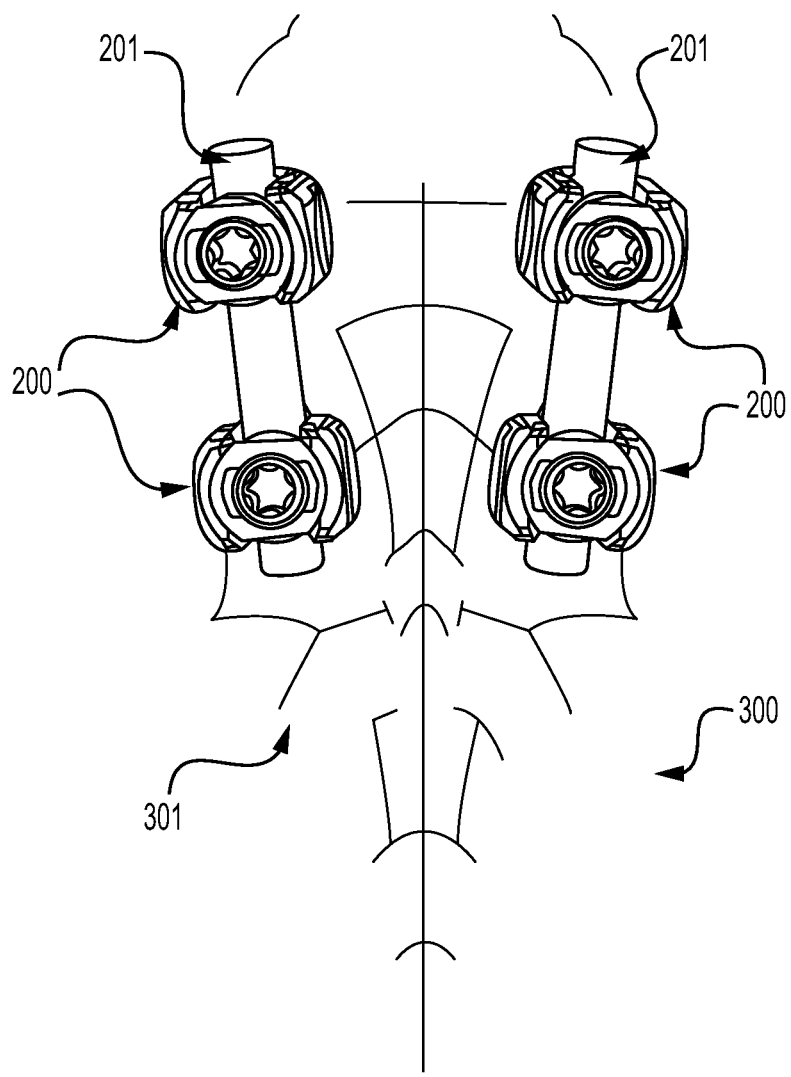
FIGS. 10A and 10B depict isometric views of monoaxial-uniplanar hybrid screw assemblies, including spinal rods received therein, installed into a bone structure, according to some methods.
Figure 10B:
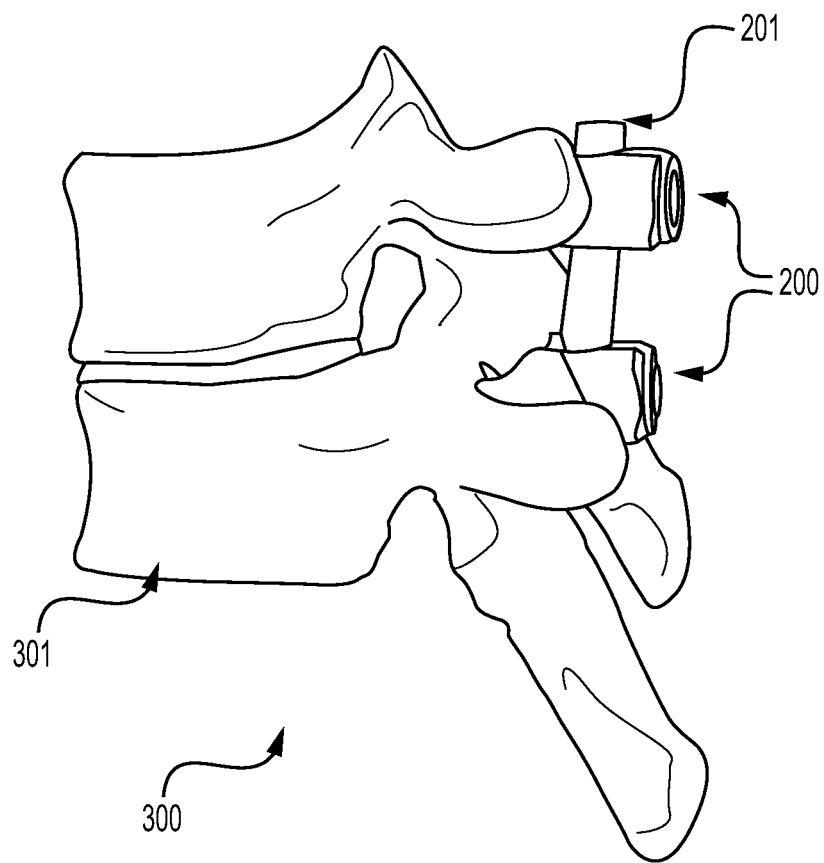

FIGS. 10A and 10B depict isometric views of monoaxial-uniplanar hybrid screw assemblies, including spinal rods received therein, installed into a bone structure, according to some methods. FIG. 10A depicts an isometric front view of two (2) pair of monoaxial-uniplanar hybrid screw assemblies 200, with spinal rods 201 positioned and secured therein, installed into a bone structure 301, according to some embodiments. FIG. 10B depicts an isometric side view of a pair of monoaxial-uniplanar hybrid screw assemblies 200, with a spinal rod 201 positioned and secured therein, installed into a bone structure 301, according to some embodiments.

Although specific embodiments have been described above, these embodiments are not intended to limit the scope of the present disclosure, even where only a single embodiment is described with respect to a particular feature. Examples of features provided in the disclosure are intended to be illustrative rather than restrictive unless stated otherwise. The above description is intended to cover such alternatives, modifications, and equivalents as would be apparent to a person skilled in the art having the benefit of this disclosure.

The scope of the present disclosure includes any feature or combination of features disclosed herein (either explicitly or implicitly), or any generalization thereof, whether or not it mitigates any or all of the problems addressed herein. Various advantages of the present disclosure have been described herein, but embodiments may provide some, all, or none of such advantages, or may provide other advantages.

What is claimed is:

1. A spinal rod anchoring device comprising:
   a body comprising a distal end and a proximal end, wherein a threaded bone anchor extends along a longitudinal axis and is positioned toward the distal end, and a U-shaped head portion is positioned toward the proximal end, wherein the head portion is formed by a concave base with an extension on each end of the concave base, wherein the head portion and the threaded bone anchor are attached to one another;
   a saddle comprising a convex curvature at its lower surface and a concave interior region, wherein the interior region has an open channel therewithin, wherein the convex curvature of the saddle is slidably seated within the concave base of the head portion for arcuate sliding movement of the saddle relative to the head portion, wherein the open channel is sized to allow at least a portion of the saddle to extend beyond the head portion during the arcuate sliding movement and wherein a spinal connection element is configured to be disposed on the saddle; and
   a retaining pin configured to be inserted along the longitudinal axis through the open channel in the saddle and secured in a groove, wherein the groove is centrally positioned within the head portion, wherein the retaining pin slidably secures the saddle to the head portion; wherein the saddle rotates about a single axis and angulates the spinal connection element about the single axis thereof.

2. The spinal rod anchoring device of claim 1 further comprising a closure mechanism configured to be positioned within the head portion.

3. The spinal rod anchoring device of claim 2, wherein the closure mechanism locks the spinal connection element and the saddle in an angulation relative to the body about the single axis.

4. The spinal rod anchoring device of claim 1, wherein the retaining pin comprises a proximal end and a distal end, wherein the retaining pin comprises a conical taper at the proximal end and two or more wire slits at the distal end.

5. The spinal rod anchoring device of claim 4, wherein the retaining pin further comprises an extension disposed about at least a portion of the distal end.

6. The spinal rod anchoring device of claim 1, wherein the retaining pin is configured to flex into the groove positioned within the head portion.

7. The spinal rod anchoring device of claim 1, wherein the groove extends toward the distal end of the body.

8. The spinal rod anchoring device of claim 1, wherein the head portion is configured to movably seat the saddle, and wherein the saddle and the head portion comprise two matching radii.

9. The spinal rod anchoring device of claim 1, wherein the saddle further comprises an upper surface profile and a lower surface profile, wherein the profile of the upper surface compliments the profile of the spinal connection element.

10. The spinal rod anchoring device of claim 9, wherein the lower surface profile of the saddle compliments the base of the head portion upon which the saddle is seated.

11. The spinal rod anchoring device of claim 1, wherein the saddle comprises a convex lower surface.

12. A spinal rod anchoring device comprising:
    a body comprising a distal end and a proximal end, wherein a threaded bone anchor extends along a longitudinal axis and is positioned toward the distal end, and a U-shaped head portion is positioned toward the proximal end, wherein the head portion and the threaded bone anchor are fixedly attached;
    a saddle comprising a convex curvature at its lower surface and a concave interior region, wherein the interior region has an open channel therewithin, wherein the convex curvature of the saddle is slidably seated within a concave base of the head portion for arcuate sliding movement of the saddle relative to the head portion, wherein the open channel is sized to allow at least a portion of the saddle to extend beyond the head portion during the arcuate sliding movement and wherein a spinal connection element is configured to be disposed on the saddle, the concave base and the convex curvature of the lower surface restricting movement of the saddle along a single plane; and
    a retaining pin configured to be inserted along the longitudinal axis through the open channel in the saddle and secured in a groove, wherein the groove is centrally positioned within the base of the head portion, wherein the retaining pin slidably secures the saddle to the head portion;
a closure mechanism configured to be positioned within the head portion;
wherein the saddle and the head portion comprise two matching radii, wherein the saddle rotates about a single axis and angulates the spinal connection element about the single axis thereof, and wherein the closure mechanism locks the spinal connection element and the saddle in an angulation relative to the body about the single axis;
wherein the U-shaped head portion includes channels disposed about side surfaces of the extensions.

13. The spinal rod anchoring device of claim 12, wherein the retaining pin comprises a proximal end and a distal end, wherein the retaining pin comprises a conical taper at the proximal end and two or more wire slits at the distal end.

14. The spinal rod anchoring device of claim 13, wherein the retaining pin further comprises an extension disposed about at least a portion of the distal end.

15. The spinal rod anchoring device of claim 12, wherein the retaining pin is configured to flex into the groove positioned within the head portion.

16. The spinal rod anchoring device of claim 12, wherein the groove extends toward the distal end of the body.

17. The spinal rod anchoring device of claim 12, wherein the saddle further comprises an upper surface profile and a lower surface profile, wherein the profile of the upper surface compliments the profile of the spinal connection element.

18. The spinal rod anchoring device of claim 12, wherein the saddle comprises a convex lower surface.

19. A method comprising:
fastening two or more spinal rod anchoring devices into two or more vertebrae, wherein each spinal rod anchoring device comprises:
a body comprising a distal end and a proximal end, wherein a threaded bone anchor extends along a longitudinal axis and is positioned toward the distal end, and a U-shaped head portion is positioned toward the proximal end, wherein the head portion and the threaded bone anchor are fixedly attached;
a saddle comprising a convex curvature at its lower surface and a concave interior region, wherein the interior region has an open channel therewithin, wherein the convex curvature of the saddle is slidably seated within a concave base of the head portion for arcuate sliding movement of the saddle relative to the head portion, wherein the open channel is sized to allow at least a portion of the saddle to extend beyond the head portion during the arcuate sliding movement and wherein a spinal connection element is configured to be disposed on the saddle;
a retaining pin configured to be inserted along the longitudinal axis through the channel in the saddle and secured in a groove, wherein the groove is centrally positioned within the base of the head portion, wherein the retaining pin slidably secures the saddle to the head portion;
a closure mechanism configured to be positioned within the head portion;
positioning the spinal connection element about a single axis relative to the body of a first spinal rod anchoring device, wherein the positioning comprises translating and angulating the saddle within the head portion;
positioning the spinal connection element attached to the first spinal rod anchoring device and;
interconnecting at least a second rod anchoring device with the spinal connection element;
wherein the U-shaped head portion includes channels disposed about side surfaces of the extensions.

20. The method of claim 19, wherein the saddle and the head portion comprise two matching radii, wherein the saddle rotates about a single axis and angulates the spinal connection element about the single axis thereof, and wherein the closure mechanism locks the spinal connection element and the saddle in an angulation relative to the body about the single axis.

* * * * *